US011328514B2

(12) United States Patent
Vancraybex et al.

(10) Patent No.: US 11,328,514 B2
(45) Date of Patent: May 10, 2022

(54) CENTRALIZED MONITORING OF CONFINED SPACES

(71) Applicant: Total Safety U.S., Inc., Broussard, LA (US)

(72) Inventors: Gunter Jano Emiel Vancraybex, Bilzen (BE); Dusan Rakic, Hillegom (NL); Jeremy Daniel St. Germain, Youngsville, LA (US); Binu Oommen Joy, Houston, TX (US)

(73) Assignee: Total Safety U.S., Inc., Houston, TX (US)

( * ) Notice: Subject to any disclaimer, the term of this patent is extended or adjusted under 35 U.S.C. 154(b) by 300 days.

(21) Appl. No.: 16/507,767

(22) Filed: Jul. 10, 2019

(65) Prior Publication Data

US 2020/0019791 A1    Jan. 16, 2020

Related U.S. Application Data

(60) Provisional application No. 62/696,695, filed on Jul. 11, 2018.

(51) Int. Cl.
*G06V 20/52* (2022.01)
*G01N 33/00* (2006.01)
(Continued)

(52) U.S. Cl.
CPC ......... *G06V 20/52* (2022.01); *G01N 33/0075* (2013.01); *G06F 3/04886* (2013.01);
(Continued)

(58) Field of Classification Search
None
See application file for complete search history.

(56) References Cited

U.S. PATENT DOCUMENTS 9,612,195 B1    4/2017  Friedman
10,060,200 B2   8/2018  Rice, II
(Continued)

FOREIGN PATENT DOCUMENTS

WO       2016081821 A1      5/2016
WO   WO-2016081821 A1 *    5/2016    ......... G08B 21/0453
(Continued)

OTHER PUBLICATIONS

Extended European Search Report issued in corresponding European application No. 19185534.5 dated Dec. 13, 2019 (10 pages).
(Continued)

*Primary Examiner* — Kaitlin A Retallick
(74) *Attorney, Agent, or Firm* — Ferguson Braswell Fraser Kubasta PC

(57) ABSTRACT

A method that includes receiving a data stream from point monitoring cases proximate to confined spaces, the data stream include at least on camera feed of the confined space, generating a display from the data stream for a single display device, wherein the display comprises a tile view including a tile for each confined space of confined spaces being monitored. The tile includes at least one camera feed from a camera located at the confined space, a number of workers in proximity to the confined space, wherein the number of workers is displayed in the tile above the at least one camera feed, control buttons located in the tile to a right of the at least one camera feed, and gas sensor indicators located in the tile.

20 Claims, 35 Drawing Sheets

(51) Int. Cl.
*G06F 3/04886* (2022.01)
*G06V 20/00* (2022.01)
*G06V 20/40* (2022.01)
*G06V 40/10* (2022.01)

(52) U.S. Cl.
CPC .............. *G06V 20/36* (2022.01); *G06V 20/40* (2022.01); *G06V 40/10* (2022.01)

(56) References Cited

U.S. PATENT DOCUMENTS

| | | | |
|---|---|---|---|
| 2002/0027502 A1* | 3/2002 | Mayor | G08B 25/14 340/431 |
| 2006/0104312 A1* | 5/2006 | Friar | G08B 1/08 370/506 |
| 2007/0188318 A1 | 8/2007 | Cole et al. | |
| 2007/0285222 A1 | 12/2007 | Zadnikar | |
| 2008/0284579 A1 | 11/2008 | Contreras | |
| 2009/0309465 A1* | 12/2009 | Quirico | G21F 5/015 312/209 |
| 2010/0232644 A1* | 9/2010 | Hsiao | G06K 9/00771 382/103 |
| 2011/0118561 A1* | 5/2011 | Tari | A61B 5/742 600/301 |
| 2013/0229278 A1* | 9/2013 | Davis | G08B 21/24 340/521 |
| 2016/0044282 A1* | 2/2016 | Veluchamy | H04N 5/23206 348/14.04 |
| 2016/0078698 A1 | 3/2016 | Moses et al. | |
| 2017/0097621 A1* | 4/2017 | Ackmann | G05B 19/0426 |
| 2017/0236397 A1 | 8/2017 | Myslenski et al. | |
| 2017/0248681 A1 | 8/2017 | Johnson et al. | |
| 2017/0254788 A1 | 9/2017 | Baldaccini | |
| 2017/0351923 A1* | 12/2017 | Rice, II | G07C 9/30 |
| 2018/0030759 A1 | 2/2018 | Chanbonpin | |
| 2018/0289346 A1* | 10/2018 | Van Beek | A61B 6/4441 |
| 2019/0200872 A1* | 7/2019 | Matsuoka | A61B 5/0013 |

FOREIGN PATENT DOCUMENTS

| | | |
|---|---|---|
| WO | 2017204642 A1 | 11/2017 |
| WO | 2017210480 A1 | 12/2017 |
| WO | 2018045059 A1 | 3/2018 |
| WO | 2018068130 A1 | 4/2018 |

OTHER PUBLICATIONS

Confined Space Entry; <https://www.raesystems.com/solutions/confined-space-entry>; Accessed Aug. 15, 2018 (3 pages).
Solution Brief: Rice Electronics Connected Worker Solution with Intel IoT Technology; <https://www.intel.com/content/dam/www/public/us/en/documents/solution-briefs/rice-connected-worker-solution-brief.pdf>; Accessed Aug. 15, 2018 (3 pages).

* cited by examiner

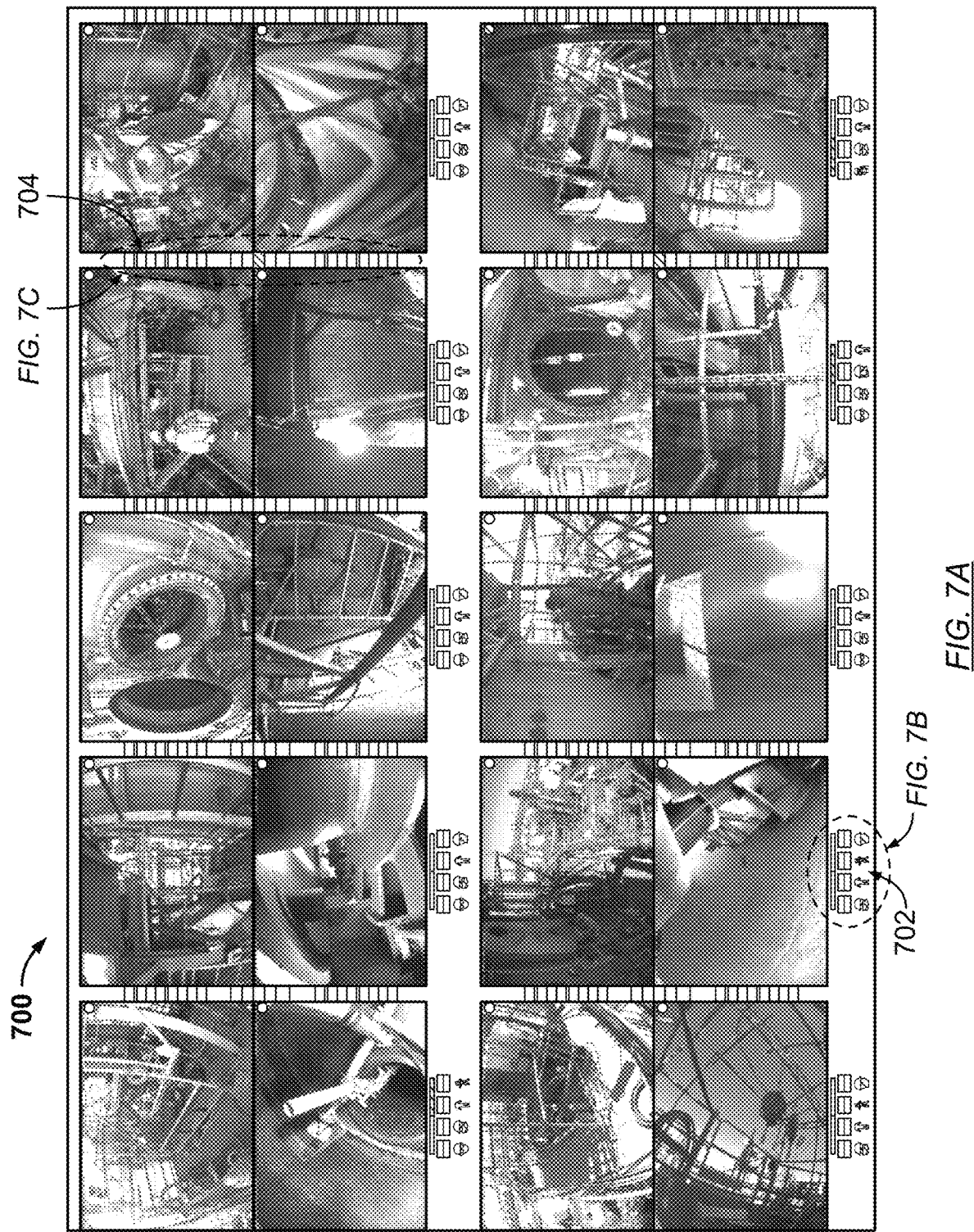

1000

| Incident Report | | |
|---|---|---|
| Safety Observation | | |
| Reported To | Employee A | ←—1002 |
| Role | Technician | ←—1004 |
| Nature Observation | Safety | ←—1006 |
| Involved Party | Gas Company X | ←—1008 |

Cancel | Next

Incident Report

Safety Observation

Why did it happen?

| Why? | Helmet annoying to work with |
| Why? | Helmet blocks view |
| Why? | Impossible to reach head into tight space |
| Why? | No aware of safety rules |
| Why? | |

} 1012

Comment

Back | Next ←—1014

*FIG. 10B*

Incident Report

Safety Observation — 1020

Personal Factors

- [x] Not following the safety procedures and work processes is tolerated or accepted
- [ ] Following the safety / procedures and work processes costs more time / attention
- [x] Worker is not aware of getting into a higher risk
- [ ] By not apply / deviating from the procedure or rules
- [ ] Due to insufficient attention

Environmental Factors — 1022

- [ ] Lack of or inadequate operating procedures of rules
- [ ] Inadequate communications about expectations regarding procedures or rules
- [ ] Inappropriate choice or design of tools or environment 1024:
| | |
|---|---|
| Origin | Origin of observation |
| Action Advised | Wear helmet at all times |
| Action Taken | Advised worker to wear helmet |
| Timing | 23:00 13/5/2019 |
| Ultimate Result | Safer work conditions |

[Back] [Next] — 1026

| | |
|---|---|
| System Check: 20190513-2101 | |
| Project: T201 MIDDLE | |
| Date: 5/13/2019 | Time: 8:57 PM |
| Operator: Admin | CCR-No.: 22 |

| Safe Card Reporting Near Accident & Unsafe Situation | | | |
|---|---|---|---|
| Date: | 5/13/2019 | Time: | 9:01:48 PM |
| Location: | T201 MIDDLE | Country: | Belgium |
| Notifier: | Admin | Role: | Admin |
| Reported To: | | Role: | Technician |
| NATURE OBSERVATION UNDESIRABLE CIRCUMSTANCES | | | |
| | | | |
| Involved Party: | | | |
| Description of the situation | | | |
| | | | |
| Why did it happen? | | | |
| Why | | | |
| Why | | | |
| Why | | | |
| Why | | | |
| Why | | | |
| Table of Basic Causes | | | |

| Personal Factors | Answer |
|---|---|
| Not following the safety procedures & work processes is tolerated or accepted | No |
| Following the safety procedures & work processes costs more time / attention | Yes |
| Worker is not aware of getting into an higher risk | Yes |
| By not applying / deviation from the procedure of rules | No |
| Due to insufficient attention | No |
| Environmental Factors | |
| Lack of inadequate operating procedures or rules | No |
| Inadequate communications about expectations regarding procedures or rules | Yes |
| Inappropriate choice or design of tools or equipment / failure of tools or equipment | No |

| Origin |
|---|
| Origin of Incident |

System Check: 20190513-2101
Project: T201 MIDDLE
Date: 5/13/2019     Time: 8:57 PM
Operator: Admin     CCR-No.: 22

| Name | Company | Entry Time |
|---|---|---|
| Person A | Firm A | 14:46 |
| Person B | Firm B | 15:12 |
| Person C | Firm A | 15:14 |

1160 ⟶

| System Check: 2 |
| Project: T201 TOP |
| Date: 5/13/2019    Time: 8:13 PM |
| Operator: Admin    CCR-No.: 22 |

Step 1: Gas

CO ☑     H2S ☑
LEL ☑     O2 ☑
Tubing ☑     Flow ☑

| CO | H2S | LEL | O2 |
| 0 | 0 | 0 | 20.9 |

Comments

Step 2: ACU

ACU ☑
Reader IN ☑    0      Reader OUT ☐    Missing
Comments

Step 3: Cameras

Camera IN ☑
Camera OUT ☑
NAS ☑
Camera History ☑

Inside      Outside

Comments

1162

| |
|---|
| System Check: 2 |
| Project: T201 TOP |
| Date: 5/13/2019  Time: 8:13 PM |
| Operator: Admin  CCR-No.: 22 |

| Step 4: InterCom |
|---|
| SoftPhone ☑<br>ICom IN ☑<br>ICom Out ☑<br>Comments |
| Step 5: Cables & Lables |
| Cables ☑<br>Area Monitored ☑<br>Earthing Clamp ☑<br>Nice and Tidy ☑<br>Comments |

Bump Test ID: 20190513-2051
Project: T201 MIDDLE
Date: 5/13/2019    Time: 8:48 PM
Operator: Admin    CCR-No.: 22

| Step 1: Nominal |
|---|

CO ☑         H2S ☑
LEL ☑        O2 ☑

Comments

| Step 2: Preparation |
|---|

CO   Nominal           H2S    Nominal
LEL  Nominal           O2     Nominal
Flow ☑                 Tubing ☑
Alarm Off ☑
Comments

| Step 3: BumpTest |
|---|

CO ☑         H2S ☑
LEL ☑        O2 ☑
Correct Alarm ☑

Comments

| Step 4: Final |
|---|

CO ☑         H2S ☑
LEL ☑        O2 ☑
Alarm Sounded ☑

Comments

SPM4 Gas Detection - Set 147

| | Sensor 1 | Sensor 2 | Sensor 3 | Sensor 4 | Sensor 5 | Sensor 6 |
|---|---|---|---|---|---|---|
| Sensor Type: | TOX | TOX | LEL | PID | OXY | No Sensor |
| Gas Type: | CO | H2S | CH4 | BENZENE | O2 | |
| Sensor Value: | 0 PPM | 0.7 PPM | 0 %LEL | 3.6 PPM | 20.8 %VOL | |
| Alarm Level Low: | 25 PPM | 2.5 PPM | 10 %LEL | 3 PPM | 19.5 %VOL | |
| Alarm Level High: | 50 PPM | 5 PPM | 10 %LEL | 3 PPM | 21.5 %VOL | |
| STEL Reading: | 0 PPM | 0.7 PPM | 0 %LEL | 3.6 PPM | 0 %VOL | |
| STEL Alarm Threshold: | 50 PPM | 10 PPM | 0 %LEL | 6 PPM | 0 %VOL | |
| TWA Reading: | 0 PPM | 0.1 PPM | 0 %LEL | 2.9 PPM | 0 %VOL | |
| TWA Alarm Threshold: | 25 PPM | 5 PPM | 0 %LEL | 3 PPM | 0 %VOL | |
| Peak Reading: | 0 PPM | 0 PPM | 0 %LEL | 53.7 PPM | 0 %VOL | |
| Operating Time: | 144.66 Hrs | 144.66 Hrs | 144.71 Hrs | 144.32 Hrs | 144.65 Hrs | |

1340 → (Sensor 6)
1342 → (Sensor 3)
1344 → (Toggle Sound)
1346 → (Settings)

Flow Rate: Normal
Operating Status: Running
Temperature: 24°C

[Alarm Light OFF] [Toggle Light]
[Alarm Sound OFF] [Toggle Sound]
[Alarm OFF] [Alarm ON]

[Graph] [Settings]

*FIG. 13F*

SPM4 Gas Detection - Set 147 — 1350

| | Sensor 1 | Sensor 2 | Sensor 3 | Sensor 4 | Sensor 5 | Sensor 6 |
|---|---|---|---|---|---|---|
| Sensor Type: | TOX | TOX | LEL | PID | OXY | No Sensor |
| Gas Type: | CO | H2S | CH4 | BENZENE | O2 | |
| Sensor Value: | 0 PPM | 0.8 PPM | 0 %LEL | 3.5 PPM | 20.8 %VOL | |
| Alarm Level Low: | 25 PPM | 2.5 PPM | 10 %LEL | 3 PPM | 19.5 %VOL | |
| Alarm Level High: | 50 PPM | 5 PPM | 10 %LEL | 3 PPM | 21.5 %VOL | |
| STEL Reading: | 0 PPM | 0.7 PPM | 0 %LEL | 3.6 PPM | 0 %VOL | |
| STEL Alarm Threshold: | 50 PPM | 10 PPM | 0 %LEL | 6 PPM | 0 %VOL | |
| TWA Reading: | 0 PPM | 0.1 PPM | 0 %LEL | 2.9 PPM | 0 %VOL | |
| TWA Alarm Threshold: | 25 PPM | 5 PPM | 0 %LEL | 3 PPM | 0 %VOL | |
| Peak Reading: | 0 PPM | 0 PPM | 0 %LEL | 53.7 PPM | 0 %VOL | |
| Operating Time: | 144.8 Hrs | 144.8 Hrs | 144.84 Hrs | 144.46 Hrs | 144.79 Hrs | |
| Reset All Peak Values | Reset Peak | Reset Peak | Reset Peak | Reset Peak | Reset Peak | Reset Peak |
| Graph Max Limit: | 200 ◁▷ | 100 ◁▷ | 100 ◁▷ | 1000 ◁▷ | 25 ◁▷ | 20 ◁▷ |
| Multiplier Alarm Settings: | x1 | x10 | x1 | x10 | x10 | x1 |
| Set Alarm Level Low: | 25 ◁▷ | 25 ◁▷ | 10 ◁▷ | 30 ◁▷ | 195 ◁▷ | 0 ◁▷ |
| Set Alarm Level High: | 50 ◁▷ | 50 ◁▷ | 10 ◁▷ | 30 ◁▷ | 215 ◁▷ | 0 ◁▷ |
| Set Alarm Level STEL: | 50 ◁▷ | 100 ◁▷ | 0 ◁▷ | 60 ◁▷ | 0 ◁▷ | 200 ◁▷ |
| Set Alarm Level TWA: | 25 ◁▷ | 50 ◁▷ | 0 ◁▷ | 30 ◁▷ | 0 ◁▷ | 0 ◁▷ |

☑ Set graph maximum limits manually — 1352

Flow Rate: Normal  
Operating Status: Running  
Temperature: 24°C

[Graph] [Zero] [Back]

CENTRALIZED MONITORING OF CONFINED SPACES

CROSS REFERENCE TO RELATED APPLICATIONS

The present application claims priority under 35 U.S.C. § 119(e) to U.S. Provisional Application No. 62/696,695, filed on Jul. 11, 2018, having at least one of the same inventors as the present application, and entitled, "CENTRALIZED CONFINED SPACE MONITORING SYSTEM." U.S. Provisional Application No. 62/696,695 is incorporated herein by reference.

BACKGROUND

A confined space is a space with limited in number and size of entry and exit locations and is not suitable for human inhabitants. A confined space is large enough for a human to enter and perform one or more tasks but is not designed to be continually occupied because of hazards of the confined space. Because of the limited size in a confined workspace, the limited ingress and egress locations, and various hazards within the confined space, operating within such a confined space is dangerous. As such, a need exists to provide a monitoring solution for workers in the confined space.

SUMMARY

In general, in one aspect, embodiments relate to a system that includes confined space internal monitoring devices configured to acquire monitoring data from a confined space, a point monitor case include point monitoring case ports configured to be electrically coupled to confined space internal monitoring devices, and a centralized monitoring station cabinet configured to be communicatively connected to the point monitor case. The centralized monitoring station cabinet includes a display, a processor, and a centralized monitoring application configured to execute on the processor and include a local user interface. The local user interface includes for each confined space of confined spaces being monitored an instruction to display a number of workers in proximity to the confined space, an instruction to display at least one camera feed from a camera located at a confined space, an instruction to display control buttons configured to control confined space internal monitoring devices, and an instruction to display gas sensor indicators.

In general, in one aspect, embodiments relate to a centralized monitoring station cabinet that includes a network interface connection to connect to point monitoring cases located in proximity to confined spaces and connected to confined space internal monitoring devices, a processor, and a centralized monitoring application configured to execute on the processor and include a local user interface. The local user interface includes for each confined space of confined spaces being monitored an instruction to display a number of workers in proximity to the confined space, an instruction to display at least one camera feed from a camera located at the confined space, an instruction to display control buttons configured to control confined space internal monitoring devices, and an instruction to display gas sensor indicators.

In general, in one aspect, embodiments relate to a method that includes receiving a data stream from point monitoring cases proximate to confined spaces, the data stream include at least on camera feed of the confined space, generating a display from the data stream for a single display device, wherein the display comprises a tile view including a tile for each confined space of confined spaces being monitored. The tile includes at least one camera feed from a camera located at the confined space, a number of workers in proximity to the confined space, wherein the number of workers is displayed in the tile above the at least one camera feed, control buttons located in the tile to a right of the at least one camera feed, and gas sensor indicators located in the tile.

Other aspects of the invention will be apparent from the following description and the appended claims.

BRIEF DESCRIPTION OF DRAWINGS

FIGS. 7A, 7B, and 7C shows an example interface in accordance with one or more embodiments of the invention.

FIGS. 10A, 10B, 10C, 10D, 10E, and 10F show an example interface for an incident report in accordance with one or more embodiments of the invention.

FIGS. 11A, 11B, 11C, 11D, 11E, 11F, 11G, and 11H show an example interface for a system check in accordance with one or more embodiments of the invention.

FIGS. 13A, 13B, 13C, 13D, 13E, 13F, and 13G show an example web interface in accordance with one or more embodiments of the invention.

DETAILED DESCRIPTION

Figure 1:
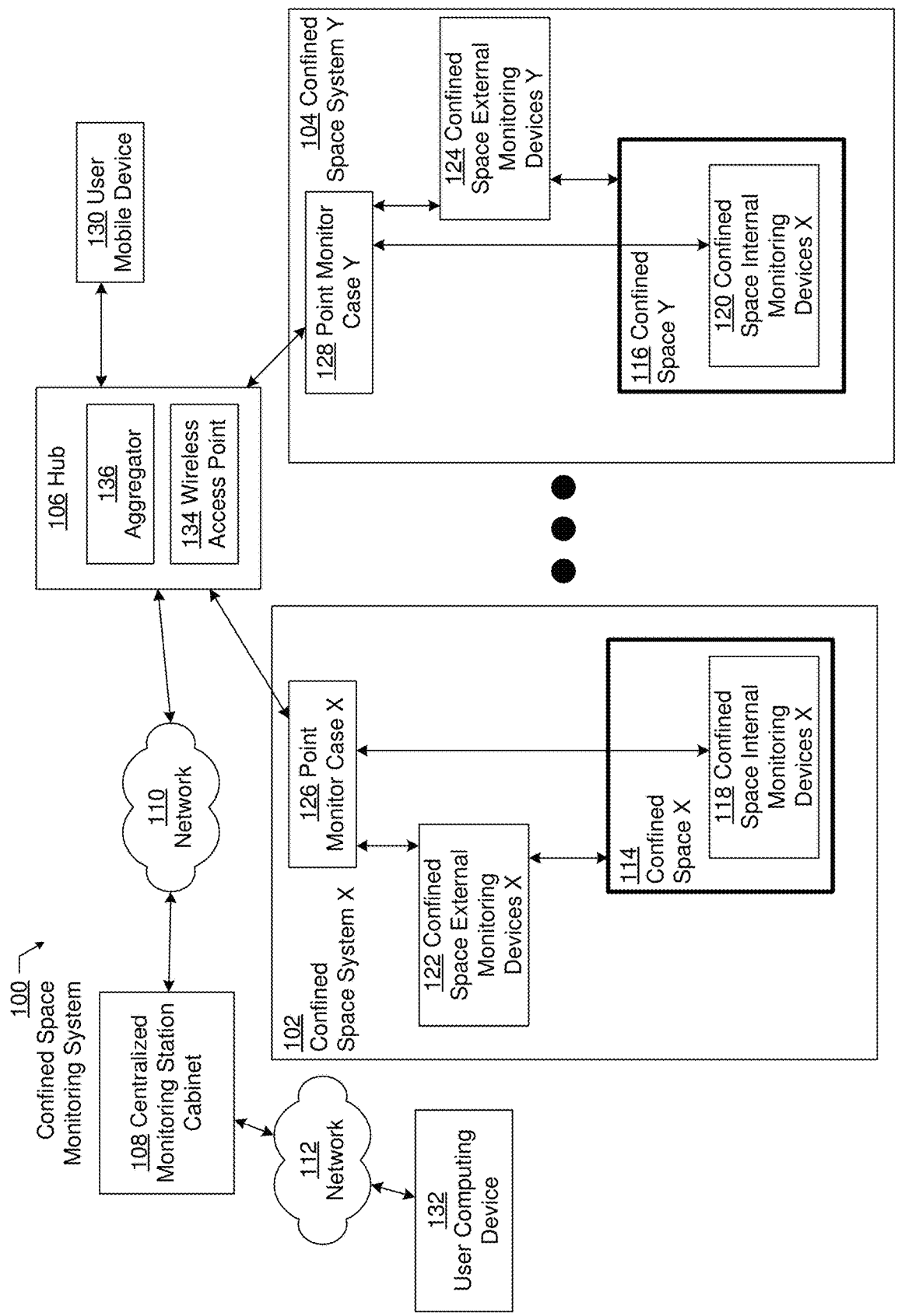
FIGS. 1, 2, 3, 4, 5, and 6 shows a diagram of a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements. Further, three collinear dots mean that more elements of the same type may optionally exist as before and after the dots. However, embodiments are not limited to the number shown for any of the elements.

In general, embodiments of the invention are directed to a centralized monitoring system for a confined space. As used throughout the application, a confined space is defined as a space with limited in number and size of entry and exit locations and is not suitable for human inhabitants. A confined space is large enough for a human to enter and perform one or more tasks but is not designed to be continually occupied because of hazards of the confined space. For example, confined spaces may be spaces that are toxic to humans, such as by having poor air quality and lack of adequate ventilation, toxic chemicals on various surface, and/or flammable, combustible material. Confined spaces may also be subject to entrapment, flooding, and other such physical hazards. Confined spaces may be a boiler, hydrocarbon and septic tank, tubing system, underground space (e.g., cave or cavern), and various other such enclosed spaces. Because of the attributes of the confined space, operating within such a confined space is a dangerous task.

The centralized monitoring system includes confined space internal monitoring devices that include sensors for obtaining measurements within the confined space. A point monitoring case is electrically connected to the confined space internal monitoring devices and gathers the readings from the confined space internal monitoring devices. For example, the point monitoring case may be located outside of the confined space and connected via wires to the confined space internal monitoring devices. Multiple point monitoring cases may exist, whereby each point monitoring case is for a different confined space. The centralized monitoring system further includes a centralized monitoring station cabinet. The centralized monitoring station cabinet is a cabinet that is communicatively connected to one or more point monitoring cases. The centralized monitoring station cabinet may be located offsite, such as in a different portion of a city, or in a different city than the point monitoring case.

The centralized monitoring station cabinet includes a display, a computer processor, and a local user interface for execution on the computer processor. For each confined space being monitored, the local user interface shows on the display the number of workers proximate to the confined space, a camera feed, gas sensor indicators, and control buttons to control, remotely, the confined space internal monitoring devices. The local user interface further shows the required personal protective equipment (PPE) for the confined space.

Turning to FIG. 1, FIG. 1 shows components of a centralized confined space monitoring system (100) in accordance with one or more embodiments. In the figures, various computing systems (e.g., user mobile device (130), user computing system (132), and various computing systems that are part of components) are described. The various computing systems may correspond to the computing systems described below and shown in FIGS. 16A and 16B. Some of the various computing systems may have display, touchscreen, keyboards, and other such user input/output devices, while other computing system are embedded systems that include functionality to process instructions and transmit results to another computing system via ports and network interface cards. The user mobile device (130) and user computing system (132) are devices that are operated by a user and not part of the centralized confined space monitoring system (100). Rather the user mobile device (130) and user computing system (132) may be separate devices that interface with one or more of the components of the centralized confined space monitoring system. In one or more embodiments, the user mobile device (130) is a device that is designed to be carried in one piece by a user, such as a laptop computer, mobile phone, tablet personal computer, and other such computing device. The user computing system (132) may be any computing device of a user regardless of whether the computing device is mobile.

As shown in FIG. 1, the confined space monitoring system (100) includes one or more confined space systems (e.g., confined space system X (102), confined space system Y (104)), a hub (106), and a centralized monitoring station cabinet (108). The one or more confined space systems are communicatively connected via wires or wirelessly to the hub (106). For example, one or more of the connections(s) between the confined space system(s) (e.g., confined space system X (102), confined space system Y (104)) and the hub (106) may be a direct electrical connection and/or a wireless packet connection. As shown in FIG. 1, the connection between the hub (106) and the centralized monitoring station cabinet (108) is via network (110). In general, a network (110) is any connected set of physical devices that is capable of transmission of data between devices. Example networks are described below in reference to FIGS. 16A and 16B. Although FIG. 1 shows two distinct networks (e.g., network (110), network (112)), the network may be the same network.

In one or more embodiments, the confined space system (e.g., confined space system X (102), confined space system Y (104)) is a system configured to monitor a single confined space (e.g., confined space X (114), confined space Y (116)). A locale may have multiple confined spaces. Each of the multiple confined spaces at a locale are connected to a hub (106) located at the locale. Thus, the hub (106) is a device interface for confined space systems that are located at the same locale. The hub (106) connects the confined space systems to the centralized monitoring station. Although not shown in FIG. 1, a hierarchy of hubs (106) may exist for a single locale.

A locale is a geographically connected region, or a sub-portion thereof owned by a same business entity in one or more embodiments. For example, the locale may be a single building, a set of connected buildings, a single processing plant, a single worksite. The locale may have a local area network (LAN). Thus, the hub (106) may be connected via the LAN of the locale to the confined space systems (e.g., confined space system X (102), confined space system Y (104)).

Returning to the discussion of the confined space system, the confined space system is a system that has some components within the confined space and some components located directly external to the confined space. The confined space system include functionality to acquire measurements and camera feed directly from the adjoining confined space, and controls access to the adjoining confined space. The camera feed is the video stream from a camera. As shown in FIG. 1, the confined space system (e.g., confined space system X (102), confined space system Y (104)) includes confined space internal monitoring devices (e.g., confined space internal monitoring devices X (118), confined space internal monitoring devices Y (120)), confined space external monitoring devices (e.g., confined space external monitoring devices X (122), confined space external monitoring devices Y (124)), and a corresponding point monitor case (e.g., point monitor case X (126), point monitor case Y (128)). The confined space internal monitoring devices and the confined space external monitoring devices are collectively referred to as monitoring devices.

The confined space internal monitoring devices are hardware devices that are physically located within the confined space. The confined space external monitoring devices are hardware devices that are physically located outside of the confined space.

Figure 2:
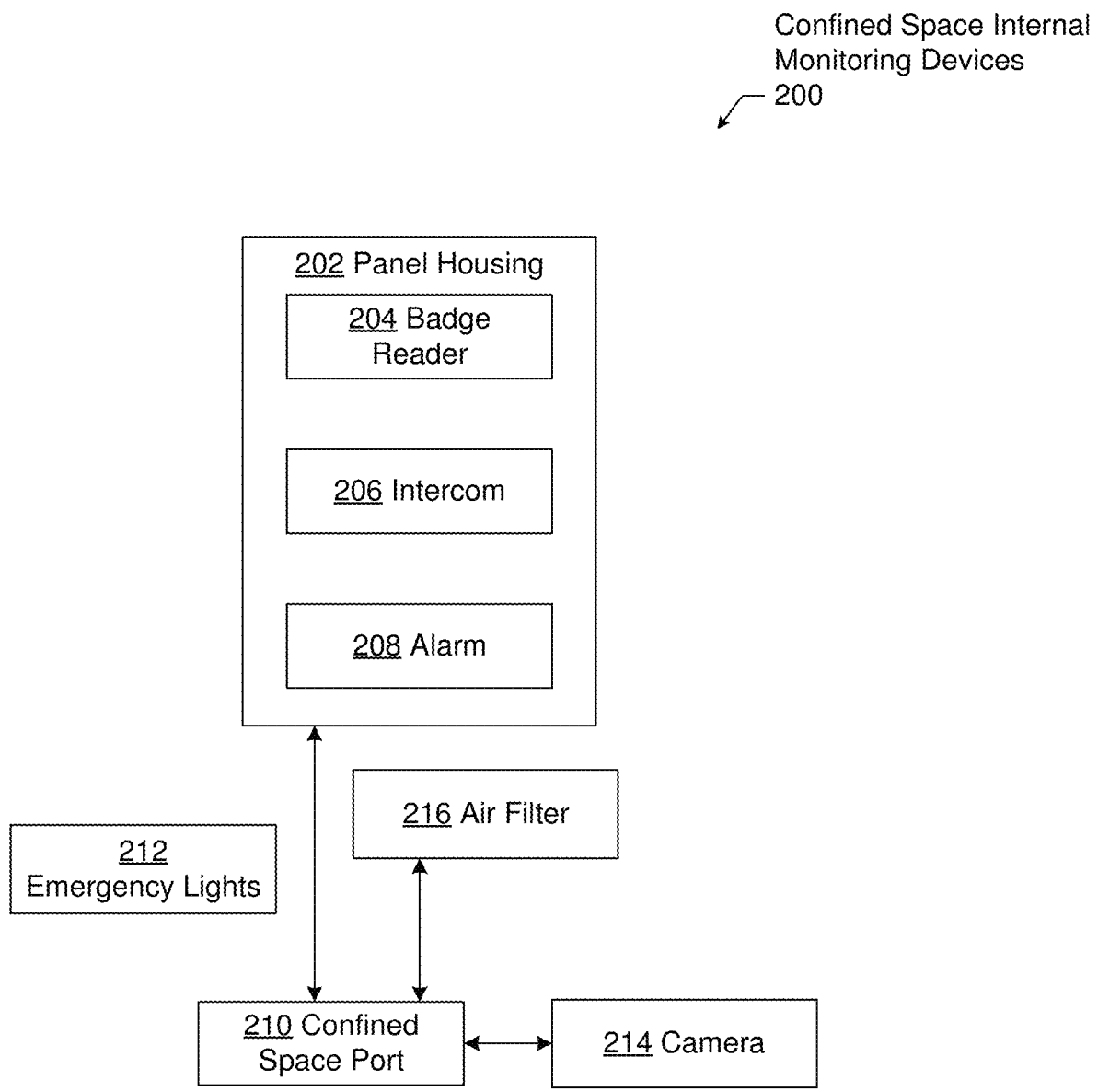

FIG. 2 shows an example diagram of confined space internal monitoring devices (200) in accordance with one or more embodiments. Specifically, the confined space internal monitoring devices are hardware devices that both control access in and out of the confined space, as well as detect hazardous conditions within the confined space.

Turning to FIG. 2, as shown in FIG. 2, the confined space internal monitoring devices (200) includes a panel having a panel housing (202). The panel housing (202) is the rigid case that surrounds and protects the inner equipment (i.e., a badge reader (204), intercom (206), and alarm (208)). The badge reader (204) is an electronic device that is configured to acquire identification data from a human or badge of a human. For example, the badge reader (204) may be a radio frequency identification (RFID) reader. Other types of badge readers may be used without departing from the scope of the invention. The intercom (206) is a communication device that includes a microphone and speaker for one way or two way communication. Through the intercom (206), a worker located within the confined space may communicate with an operator located outside of the confined space (e.g., within the confined space system, by the hub, or at the confined space monitoring cabinet). In one or more embodiments, both the intercom (206) inside and outside of the confined space will only call the operator located in the control room (e.g., at the confined space monitoring cabinet). The alarm (208) is an audio and/or visual output device that is configured to be triggered when a problem exists. For example, the alarm (208) may play a siren and/or flashing lights when triggered. As shown in FIG. 1, the badge reader (204), intercom (206), and alarm (208) are mounted within the single housing. In one or more embodiments, a single communication medium connects the panel housing (202) to the point monitor case (discussed below) via the confined space port (210) (discussed below). Moreover, the panel housing may further include a processor, memory, and communication port that are electrically coupled to the badge reader (204), intercom (206), and alarm (208). The processor, memory, and communication ports perform operations to receive instructions from the point monitor case, transmit data to the point monitor case, receive input from the badge reader, intercom, and alarm, and transmit commands/data to the badge reader, intercom, and alarm.

Continuing with FIG. 2, emergency lights (212) are lights that are configured to turn on when power is lost to the confined space. In one or more embodiments, the lights are also not connected to the port, but rather are connected to local power. The emergency lights (212) may be encased in mechanical protection, such as steel bars, to prevent breakage of the lights. An example of the emergency lights in mechanical protection is shown in FIG. 15B.

An air filter (216) is configured to acquire an air sample of the confined space. The air filter (216) may be configured to remove particulates when acquiring the air sample in order to protect gas sensors connected via tubing to the air filter (216).

The camera (214) is configured to acquire a camera feed of the inside of the confined space. The camera may be a security camera and may also include infrared functionality to obtain an image in low and no light scenarios. In one or more embodiments, the camera (214) includes a processing system to process commands and adjust the camera zoom and the camera angle, where the commands are received remotely from the point monitor case.

The camera (214), panel housing (202), and air filter (216) are connected to the point monitor case (described below in reference to FIG. 1) via a confined space port (210). The confined space port (210) is an opening in the confined space through which electrical wires may fit. Further, an air tube between the air filter (216) and the point monitor case (described below in reference to FIG. 1) may also pass through the confined space port.

Although not shown in FIG. 2, the confined space internal monitoring devices may further include a secondary audio alarm. The secondary audio alarm may be external to the panel housing (202) and internal to the confined space. Further, the secondary audio alarm may be encased in mechanical protection, such as steel housing, to prevent breakage of the speaker. An example of the secondary audio alarm is shown in FIG. 15C. Additionally, the confined space internal monitoring devices may include other sensors such as a fire detector, a smoke detector, a heat detector, and other sensors to detect hazardous conditions in the confined space.

Figure 3:
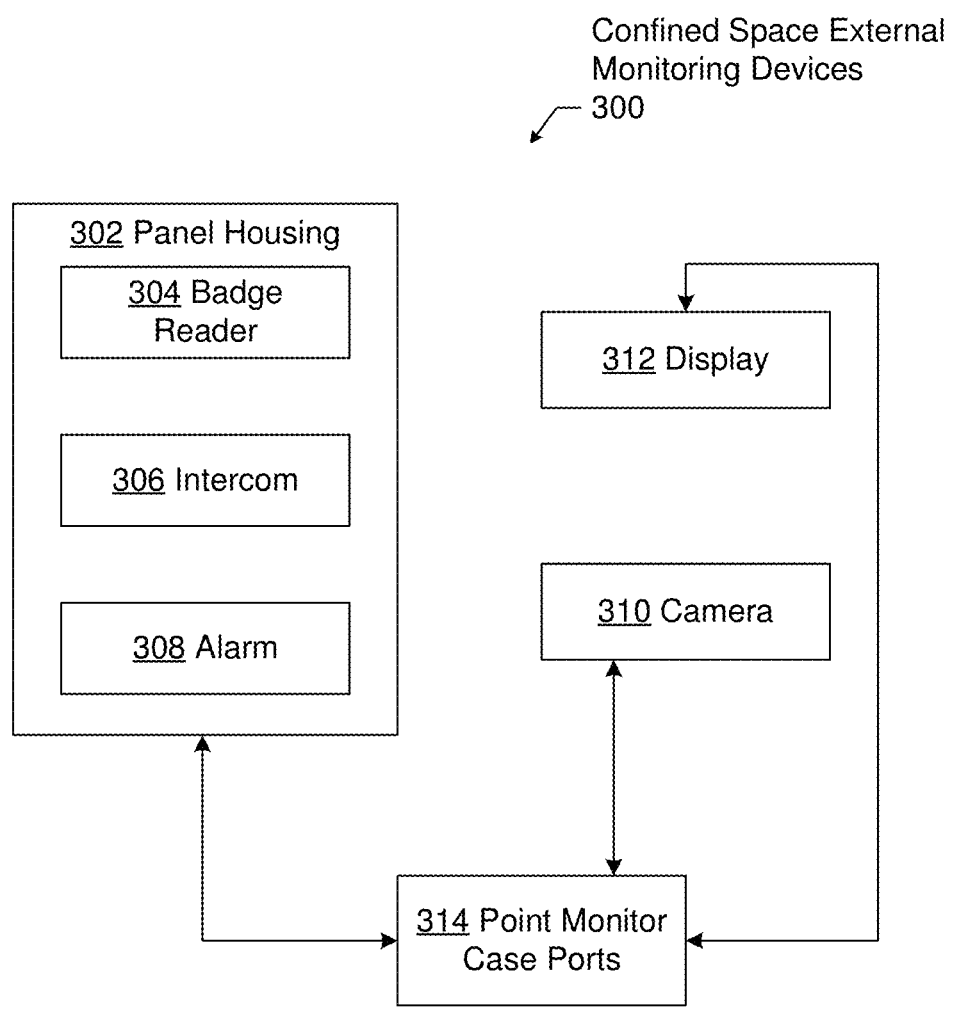

Turning to FIG. 3, FIG. 3 shows confined space external monitoring devices (300). The confined space external monitoring devices (300) are devices located on the outside of the confined space. The confined space external monitoring device (300) are devices that are directly configured to control access to the confined space and provide security for the confined space. The confined space external monitoring devices include a panel housing (302) having a badge reader (304), intercom (306), and alarm (308). The panel housing (302), badge reader (304), intercom (306), and alarm (308) may be the same or similar to the panel housing (202), badge reader (204), intercom (206), and alarm (308), respectively, described above with reference to FIG. 2.

The confined space external monitoring devices further include a camera (310) and display (312). The camera (310) may be the same or similar to the camera (214) described above with reference to FIG. 2. The display (312) is a monitor that is connected to camera (214). The display may further be a computing system, such as described below with reference to FIGS. 16A and 16B. For example, the display (312) may be a tablet personal computing (PC) device. In such a scenario, the display (312) may include functionality to create a communication channel with the centralized monitoring station cabinet and transmit audio and visual input between a user located at the display (312) and the centralized monitoring station cabinet.

The panel housing (302), camera (310), and display (312) are connected to point monitor case ports (314) on the point monitor case. The point monitor case ports (314) are hardware connections located on the point monitor case.

Returning to FIG. 1, the point monitor case (e.g., point monitor case X (126), point monitor case Y (128)) is a physical case that includes sensors and other electrical equipment for receiving data from and transmitting data to the confined space internal and external monitoring devices.

In particular, the point monitor case has gas detection sensors and an air port for receiving air from inside the confined space. The gas detection sensors include functionality to acquire an air sample from an air hose connected to the air port and detect whether a combustible or toxic gas is in the confined space. In one or more embodiments, one or more of the gas detection sensors may be specific to a type of toxic gas.

The gas detection sensors may be communicatively coupled to a computing system in the point monitor case. Specifically, the electrical equipment in the point monitor case may include a computing system for processing instructions. The computing system may include a mobile network connection, a wireless network connection, and/or other connection. Through the connection, the computing system is configured to locate and connect, wired or wirelessly, to the hub and/or to a user mobile device.

The computing system in the point monitor case interfaces with the confined space internal monitoring devices and the confined space external monitoring devices to obtain a current state of the devices (e.g., whether on/off, whether fault is detected), issue commands to the devices (e.g., change the direction and zoom state for cameras, trigger lights and alarms, unlock or lock an enclosed space based on identification received from a badge reader, etc.). The computing system in the point monitor case is further configured to execute an application that aggregates the current state from the various devices, acquires one or more readings from the one or more gas sensors, and generate a current aggregated state of the confined space. The current aggregated state may have the current state for each device with the device identifier along with a camera feed from each camera. The computing system of the point monitor case is configured to transmit, continually and/or periodically, and in accordance with a predefined protocol, the aggregated state to the hub for transmission to the centralized monitoring station cabinet.

Additionally, the application executing on the computing system of the point monitor case may include a user interface that presents the aggregated state and may be configured to receive commands to adjust one or more of the confined space internal/external monitoring devices. The user interface may be an interface of a web application transmitted to a user mobile device (e.g., user mobile device (130)) for presentation in a web browser (not shown) executing on the user mobile device (130).

Physically, the point monitor case is portable by being less than 12 inches wide, 18 inches in width, and 30 inches tall. The point monitor case has a built in trolley with wheels and a handle to roll the point monitor case to the confined space station. Further, the point monitor case may have removeable mounting hooks to hang the point monitor case on a fence or other railing.

As described above, the point monitor case is connected to a hub (106). The hub (106) is a physical computing device that includes a wireless access point (134) and an aggregator (138). The wireless access point (134) is configured to connect to a user mobile device (130). The hub may also provide an application, similar to the application of the point monitor case, with an interface for the user mobile device obtain the aggregated current state of each confined space system. The aggregated current state is the aggregated current state described above with reference to the point monitor case. Specifically, the aggregated current state includes specific gas measurements, number of people in the confined space, and others state information about the confined space. Through the wireless access point on the hub and the user's mobile device, a user may review the aggregated current state of each confined space system connected to the hub regardless of whether an independent network connection is available. The aggregator (136) is configured to aggregate the aggregated current state from each confined space system and transmit the aggregated state to the centralized monitoring station cabinet (108). In one or more embodiments, the connection between the hub (106) and the monitoring station cabinet (108) is via point to point (PTP) gigabit (GB) antennas that provide a direct connection. In other words, the hub (106) may via a single wire connect to one antenna, which transmits directly to and receives directly from a second antenna. The second antenna may be wired to the centralized monitoring station cabinet (108).

Figure 4:
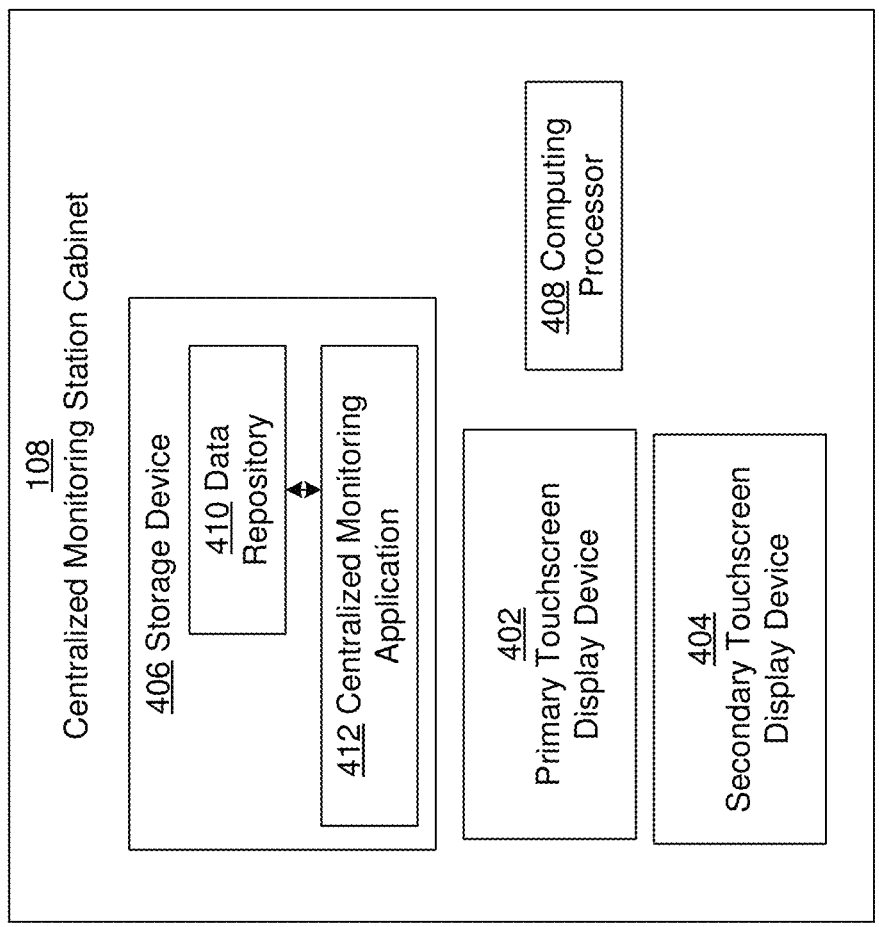

FIG. 4 shows a schematic diagram of the centralized monitoring station cabinet (108). The centralized monitoring station cabinet (108) is a cabinet that holds the confined space monitoring computing system. In the closed state, the cabinet is four feet tall, about five feet wide, and eighteen inches deep and is in the shape of a box on wheels. The top of the cabinet includes an opening from which the primary touchscreen display device (402) may roll out to sit above the cabinet. The primary touchscreen display device (402) is a display screen spanning at least ninety percent of the height and width of the cabinet, and is configured to detect touch input, such as through capacitive sensing. The primary touchscreen display device (402) is configured to display the aggregated current state of each of the confined spaces being monitored. In one or more embodiments, the interface shown on the primary touchscreen display device may concurrently show the aggregated current state of twelve confined spaces, each with at least two camera feeds.

A top portion of the front side of the confined space monitoring cabinet may fold down to form a table with front legs and the back being the cabinet itself. Inside the confined space monitoring cabinet may be one or more secondary touchscreen display devices (404). The secondary touch screen display devices may include user interfaces for guiding a user through various operations, such as creating an incident report, and performing a system test. The secondary touchscreen display devices (404) are viewable when the table is formed from the front side of the cabinet.

The centralized monitoring station cabinet (108) includes a computing system that includes a storage device (406) and a computing processor (408) for operating the touchscreen display devices and other input/output components of the computing system. The storage device (406) includes functionality to maintain a data repository (410) and a centralized monitoring application (412). The data repository (410) is any type of storage unit and/or device (e.g., a file system, database, collection of tables, or any other storage mechanism) for storing data. Further, the data repository (410) may include multiple different storage units and/or devices. The computing processor (408) is configured to execute the centralized monitoring application (412). The centralized monitoring application (412) is configured to drive the centralized monitoring station and interface with the hub and confined space systems.

Figure 5:
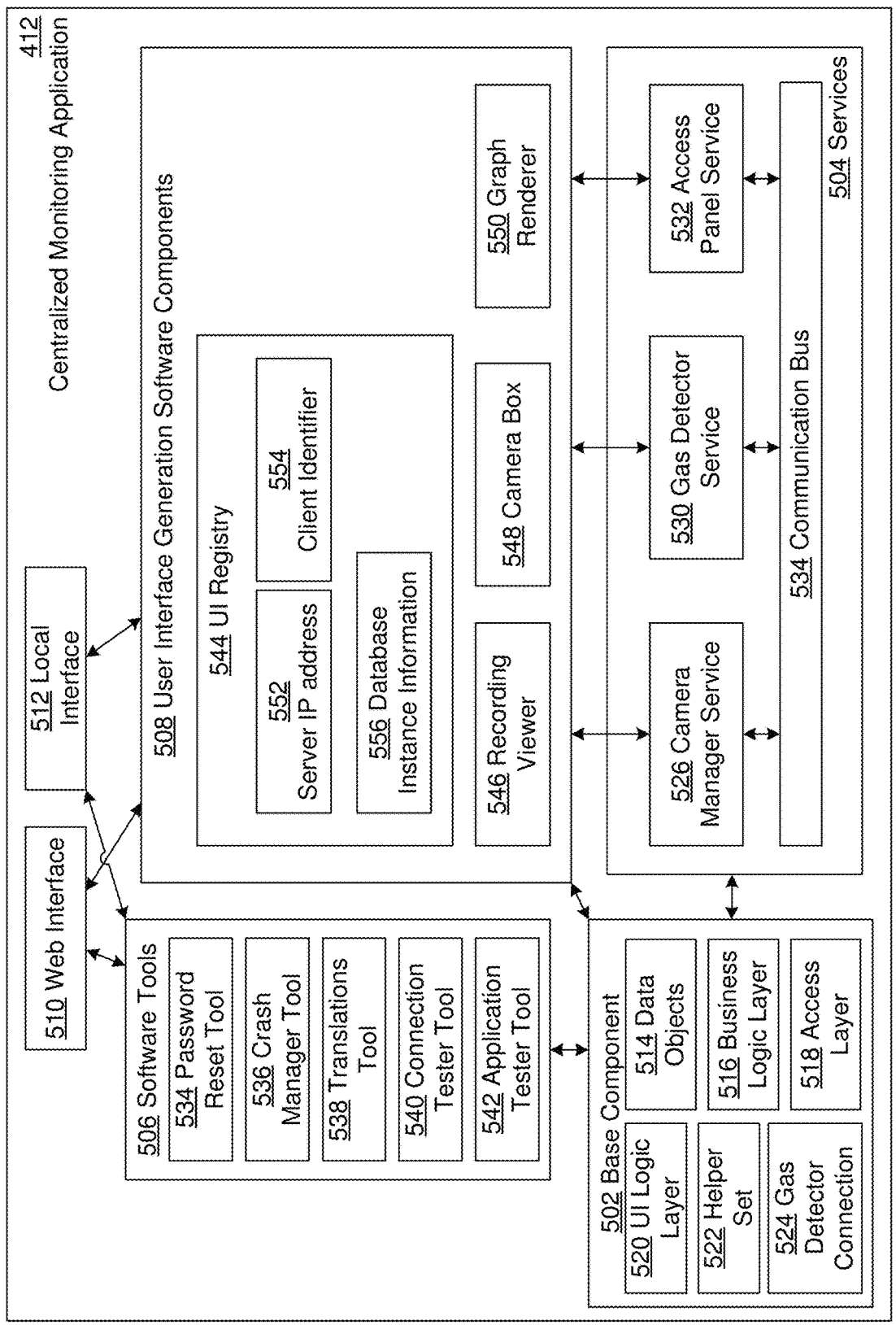

FIG. 5 shows a diagram of the centralized monitoring application (412) in accordance with one or more embodiments. As shown in FIG. 5, the centralized monitoring application (412) includes a base component (502), services (504), and software tools (506), and a user interface generation software component (508). The centralized monitoring application (412) may also include a web interface (510) and a local interface (512).

The base component (502) includes the functions on the back end of the centralized monitoring application (not involving the user interface) that enable the centralized monitoring application to execute. The base component includes dynamic objects, helpers, and other types of components that direct communication with the gas detection equipment. Additionally, the base component includes instructions to control transfer of information from a data access layer (DAL) to a business logic layer (BLL) and vice-versa for use by other components of the centralized monitoring application. The DAL has a backend of a database for the DAL to access. Specifically, the information is used by the BLL to perform the operations of the centralized monitoring application. Changes to data are changed in the user interface, sent to the BLL, which passes the changes to the BLL for writing to the database.

The services component (504) includes the services for the cameras, communication bus, gas detectors, and badge readers. The services component (504) utilizes the contents of the Base folder to create working services that can be used throughout the centralized monitoring application.

The software tools (506) includes tools that ping hardware, test database connection, add values to the machine registers, reset admin password for the centralized monitoring application, and change the language used by the centralized monitoring application.

The user interface generation software components (508) are software components that are used to generate the user interface. Specifically, the user interface generation software components (508) are front end components for connecting to the services (504) and software tools (506).

Although not shown, the centralized monitoring application (412) may include an installer. The installer may initialize the centralized monitoring application and controls how the Composite Centralized monitoring application Library components are wired to the centralized monitoring application. A user may specify a master internet protocol (IP) address of a master computing system, slave IP of the slave computing system, intended machine for install (Master PC or Slave PC), and install directory. The installer then handles installing and uninstalling the centralized monitoring application.

Below is a description of each of the components of the centralized monitoring application (412). Turning to the base component (502), the base component (502) includes the components to perform the base functionality of the centralized monitoring application. The base component includes data objects (514), a business log layer (516), a data access layer (518), a user interface (UI) logic layer (520), a helper set (522), and a gas detector connection (524).

The business logic layer (516) includes common helpers, services, and other helpers. Common helpers include the following components. Application configuration helpers create a static property with the correct type to return the new value. The application configuration helper allows the user to return a strong-typed setting by using the respective parse method. A client setting helper is a class that keeps the client settings by storing the settings dictionary and obtains the requested settings. The connection string helper is a helper class to create Entity Framework connection strings. The server settings helper is a class that retrieves server settings from the server database. The share helper class obtains the local path from share.

The services in the business logic layer (516) include an alarm manager, an archiver manager, an awareness manager, a camera manager, a client manager, a client settings manager, an export manager, an incident report manager, a gas detector siren manager, an import manager, an incident report manager, a language manager, a measurement manager, a gas detection manager, a badge reader manager, a personal protective equipment manager, a recording manager, a reset manager, a server settings manager, a set manager, a gas detector measurement acquisition manager for each different type of gas detector, a gas detector processor manager, and a user manager. Each of the aforementioned managers may be separate programming classes within the centralized monitoring application. The components of the managers are described below. The functionality provided by each of the components may be performed by individual methods in each of the classes.

The alarm manager includes methods for creating a file with specific extension representing the given alarm object, creating the alarm on file and in the database, converting the alarm object to an extensible markup language (XML) or other common format, updating the alarm document, renaming the alarm file, reading a name from the alarm file, replacing the alarm steps in the document, setting a value in the alarm file, deleting the alarm file, reading and converting the alarm file, searching for the alarm file and return a list, returning any alarm file in the database, log the existence of an alarm in the database, and perform other such operations.

The archiver manager includes components to archive measurements older than a week, day by day, delete a table with the given name, fetch measurements from the given table name, build a query to fetch the measurements for the database, fetch measurement tables from a database server and determine if the table can be archived or not, fetches the tables that have to be archived, parse the table name to fetch the date and to define if the table should be archived, and determines whether tables for the next defined number of days have been created.

The awareness manager includes functionality to obtain and save the awareness settings, add and update user awareness, and export user awareness.

The camera manager is a manager class for handling cameras from the Camera Image Recorder Service in services (504). The camera manager includes functional to return cameras connected to sets that needs recording of their images, return cameras connected to a specific set that needs recording of their images, discover the connected cameras with a Ping command, update the brand of the configured camera in the database, test for the camera brand of the discovered camera, and return the camera brand based on a name of the camera.

The client manager is a manager to manage the clients connected to the server. A client is a user computing system and the server is computing system in the centralized monitoring station cabinet in FIG. 1. The client manager includes functionality to add a client to the server application, add a set to a client to place on the canvas of the client, delete the client set for a new set, activate and deactivate a client for a set, obtain an IP address of edited clients, a single client, a subset of clients, or all clients, and update the IP address to set the updated IP address as the active IP address for the client.

The client settings manager is a class for obtaining client settings. The client settings manager includes functionality to obtain the client settings for a certain client, retrieve a setting by the settings key value, add or update a client setting record in the database, fetch the setting from the database depending on the key and client identifier (ID), reset the value of a Client Setting database record to an empty string, delete the client setting from the database, and return client settings for a particular client.

The export manager is configured to create an export file in XML format that includes client, sets, gas detectors, cameras, client settings, server settings, users. The export manager further includes functionality to the clients that represent the master and the slave, identify the last active client, create the XML export document, create a XElement that includes the settings connected to the client, creates the XElement for the cameras connected to a set, create the XElement for the gas detectors connected to a set, create the XElement for the client settings, create a XElement for the server settings, a XElement for the users, and convert user elements to XElements.

The gas detector siren manager is a manager for the client to activate and deactivate the siren connected to the Modbus gas detectors. The gas detector siren manager activates and deactivates the siren on the gas detector with the given IP address.

The import manager includes functionality to reset the centralized monitoring application and load the settings from an import file in the database. The import manager is configured to load the file in memory, check if the version in the file is the same as the version of the application (without build number), process the file and create database objects and commit them to the database, create database objects for groups and for clients. The import manager is further configured to create various database objects (e.g., ClientSet database objects, set database objects, camera database objects, GasDetector database objects, ClientSettings database objects, and user database objects). The import manager further includes functionality to create user elements.

The incident report manager obtains the incident report settings and saves the incident report settings. The incident report manager is further configured to get incident reports and saves the incident report titles and items. The language manager fetches languages.

The measurement manager is a manager for the service to handle the measurements taken by the server gas measurements application. The measurement manager includes functionality to fetch measurements between a certain timespan from a specific set for display in the graph, get graph measurements so the graphs can be written to the database, and takes a list of measurements and writes them to the database in bulk. The measurement manager includes functionality to take a list of graph measurements and write the measurements to the database in bulk. The measurement manager is further configured to create a database query string to fetch the graph measurement values from the database and create a query which returns the last graph measurements right before the actual start date.

The gas detection manager includes functionality to discover the gas detectors connected to a specific set, to recalibrate the gas detectors connected to a specific set, and to determine the type of detector.

The badge reader manager is a manager for a badge reader service. The badge reader area is an area defined for a particular badge reader, such as a particular confined space. The badge reader manager returns badge reader areas as found in a dataset, returns data from a specified badge reader area, return the total number of persons present in the specific badge reader area, builds a connection string to the badge reader database, return count data based on the specific client ID, and get a badge reader ID from a set.

The personal protective equipment manager includes functionality to get personal protective equipment from a database and save personal protective equipment for a specific set.

The recording manager includes functionality to get a recording set for the given camera set, start recording the camera images for the supplied set, check if the camera will reset during the recording and notifies the reboot time in the log, set a timer for recording in a specified time, stop recordings, and start and stop a new recording. The recording manager further includes functionality to restart the recording, and check whether the recording for a set between timestamps. The reset manager is a manager to delete information from a data repository.

The server settings manager add or update a server setting record in the database, fetch the setting from the database depending on a key, reset the value of a Server Setting database record to an empty string, delete a server setting from a database, and return the server settings.

The set manager includes functionality to handle sets from some of the services, return sets needed for the a gas detector service, return a specific set for the gas detector reader service, get the sets configured for each client, get the camera sets for the camera image reader, determine whether the sets are available for positioning, and return client sets for specific client. The set manager further includes functionality to detect sets inside the current IP range, determining whether cameras, gas detectors or badge reader cards are available. The set manager is further configured to ping the camera, detector, badge reader, and siren of a set and return the status. The set manager is further configured to saves or updates sets into the database (no sets will be removed), adds, updates and removes entries for client sets in the database, and recalibrates a set. The set manager is further configured to retrieve a set object to use in the measurement graph renderer application, delete a set, enable and disable a badge reader, and get a set for gas detector with a specific gas detector ID. The set manager further includes functionality to saves notes for sets with a specific set ID and save set groups.

The gas detector measurement acquisition manager for each different type of gas detector. Specifically, the gas detector measurement acquisition manager includes functionality to take measurements from a gas detectors, put short array into measurement, determines the type of device fault on the given gas detector, determine the type of alarm on a gas detector, determine the type of alarm on a given gas detector, and save for graph data for gas detector ID. The gas detector measurement acquisition manager is further configured to read a value, ping a gas detector, determine if an alarm is activated, check if there is a device error, and initialize a connection.

The user manager includes functionality to get users, add a user to the database, update the user, activate and deactivate a user, create a hash, make a log entry, log off a specific user, log off a user that is marked as logged on the client, close the client application. The business logic layer further includes various helper classes to write files to storage, create directory, initialize client, and perform other actions.

The user interface (UI) logic layer (520) includes getting alarm XML documents and reading them, configuring the client settings, server to client configuration, siren activation/deactivation, incident processing/reporting, screenshot management, and recording directory management. The UI logic layer includes functionality to read a specific alarm file, return a path to an alarm file, convert an alarm file into an object, hold values from the alarm file, return an object holding the values from the alarm file, and manage the client settings in the register and the connection to the server application. The UI logic layer further includes functionality to check whether the server can be reached using a ping. The UI logic layer further includes functionality to check if the server is configured in the register, can be reached with a synchronous ping. The UI logic layer is further configured to activate and deactivate the siren connected to the gas detector, such as using the IP address, perform file management for camera feed files, save and manage screenshots from camera feed files, get an incident moment for a set, parse a file, save the safety observation and the contents of the report to disk, and obtain, update, and delete, incident reports. The UI logic layer further includes functionality to create a document for the incident report, writes a moment to the document, get the background color for a gas detector, write user interface widgets, and perform other such actions. The UI logic layer further includes functionality to create a static property with the correct type to return the new value and allows the user to return a strong-typed setting by using the respective parse method.

The data access layer (518) is the layer to provide simplified access to data stored in persistent storage and performs data management. The data access layer (518) converts data objects to a data access layer representation and vice versa. The objects include alarm objects, camera objects, badge reader objects, client settings, non-audit fields, user settings, languages, and incident reports.

The helper set (522) includes helpers to read and write to registers, set connection teams, set register values get domain values, and split IP addresses.

The gas detector connection (524) includes functionality to read out the gas detector register and process the read values to a measurement object, load the gas detector set for each gas detector in the given set, loop over the stored connections and will fetch the values in the register for connections (GasDetector) a connection is lost, and to process the received values to a measurement object. The gas detector connection includes functionality to create a measurement object for a connection error measurement if the read register is null, convert the readout of the gas detector register to a measurement object, and figure out is a new value has to added in the MeasurementGraph database.

The services (504) includes a camera manager service (526), a gas detector service (530), and an access panel service (532). The various services are connected to each other via a communication bus (534). The camera manager service (526) includes functionality to create a communication bus service proxy, get cameras from a communication bus via communication bus proxy, load the directory to save the videos through the communication bus using the recording manager service, starts the camera recorder, stop recordings through the recording manager service, start stop, and restart recordings for camera sets. The camera manager service (526) further is configured to check if still recording for a set between time stamps.

The communication bus (534) includes proxies for the gas detector reader, the badge reader service, and the client service. The communication bus (534) includes functionality to perform an application reset using the base component, inform client the centralized monitoring application is reset, get areas for the client for a gas detector, for a badge reader, and camera recorder. The communication bus (534) includes functionality to get a set for a database, delete a set, sends message to the clients in the list informing that the client configuration has been changed, add a set to a database, remove a set from a client, and start and stop tracking a set. The communication bus if further configured to poll IPs of badge readers, card readers, gas detector readers, and other monitoring equipment, and to manage client and server settings. The communication bus is further configured to get a specific set for a measurement graph, get a graph image, add, update, and delete users, log users, manage languages, add, update, delete, and raise an alarm. The communication is further configured to manage a camera image recorder, handle awareness settings, set groups, manage personal protection equipment, get and save incident report settings.

The gas detector service (530) includes functionality to start gas detectors, clear gas detectors, add gas detectors, obtain measurements from gas detectors, clear a measurement buffer, clear graph queues, remove old items from a list, add and remove measurements to a set, remove a set, and restart itself.

The access panel service (532) includes functionality to create a communication bus service proxy, obtain client areas dictionary, obtain a number of confined spaces, connect to a badge reader device, obtain a number of people in a confined space, obtain a count, register and unregister a client, get count data, remove an area, and start a badge reader service to read from a database.

The software tools (506) include a password reset tool (534), a crash manager tool (536), a translations tool (538), a connection tester tool (540), and an application tester tool (542). The tool may include additional tools to perform pinging operations, test database connections, and read, write and update register values. The password reset tool (534) includes functionality to reset an administrator password reset. The crash manager tool (536) includes functionality to determine which service has crashed. The translation tool (538) translates portions of the application into a different language. The application tester tool (542) is configured to perform testing of the various monitoring devices, hub, and point monitor case (i.e., target device). The application tester tool (542) may include functionality to prompt a user to enter an IP address of a target device, and test a reset, archive a recording, get an area, and perform area testing for one or more target devices. The application tester toll (542) includes functionality to enable and disable devices and record a test. The connection tester tool (540) is configured to test connections to various target devices.

The centralized monitoring application (412) further includes a user interface generation software component (508) that includes a UI registry (544), a recording viewer (546), a camera box (548), and a graph renderer (550). The UI registry (544) is a storage location to store information about connections to devices and user interface settings. The UI registry (544) includes functionality to store a server IP address (552), a client identifier (554), and database instance information (556). The server IP address (552) is the IP address of the computing system of the centralized monitoring station application. The client identifier (554) is an identifier of a client computing device (e.g., user computing device in FIG. 1) connected to the centralized monitoring application (412). The database instance information (556) captures information describing an instance of the database having information about the various devices of the system, in accordance with one or more embodiments. Although FIG. 5 is described with respect to a database, any data repository may be used, as described in FIG. 4.

The recording viewer (546) includes functionality to obtain a recording for a camera device from storage using the services (504) and base component (502), generate a recording, and present the recording. Specifically, the recording viewer (546) is configured to display a recording player, with a start, stop, play, fast forward, rewind.

The camera box (548) includes functionality to display the current camera feed for each of the confined spaces. The graph renderer (550) includes functionality to generate a graph of measurement values (e.g., graph measurement values). To perform the aforementioned functionality, the camera box (548) and graph renderer (550) are configured to use the services (504) and the base component (502).

Continuing with FIG. 5, the centralized monitoring application (412) further includes a web interface (510) and a local interface (512). The web interface (510) is an interface that defines the layout of the UI within a web browser. Specifically, the centralized monitoring application (412) includes a web application (510) component that is accessible from a remote user computing device. The local interface (512) is the graphical user interface displayed on the display devices shown in FIG. 4. In particular, the local interface (512) may be displayed on the primary display device, and on the secondary display device of FIG. 4. Specifically, the local interface is a graphical user interface that displays the camera feeds from the confined space, number of people in the confined space, gas readings of the confined space, etc. The local interface (512) and the web interface (510) include graphical user interface widgets to guide a user through testing the confined space system, creating incident reports, and performing administrative management of the centralized monitoring application (412). In one or more embodiments, the local interface (512) and the web interface (510) may directly or indirectly communicate with the various other components of the centralized monitoring application (412) including the software tools (506), the user interface generation software components (508), the services (504), and the base component (502).

Figure 6:
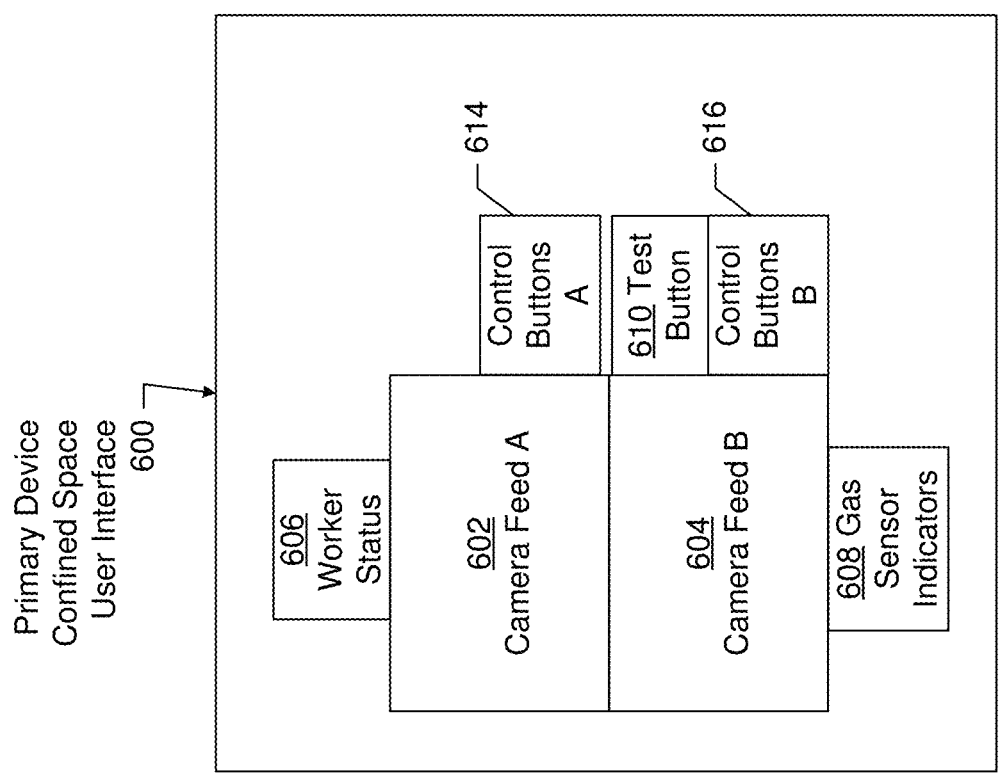

FIG. 6 shows a diagram of a primary device confined space user interface (600). As described above, the primary device confined space user interface (600) is at least a portion of the local interface of FIG. 5 that is displayed on the primary device of FIG. 4. Because of the size of the primary display device, the user interface (600) may span the width of the centralized confined space monitoring cabinet. For each confined space being monitored, the primary device confined space user interface (600) may display the components of FIG. 6 concurrently across the confined spaces. Further, the components of FIG. 6 are not shown according to scale.

As shown in FIG. 6, the user interface (600) shows at least two camera feed (e.g., camera feed A (602), camera feed B (604)) from cameras located in the confined space system. For example, at least one camera feed may be from a camera inside the confined space (e.g., showing a wide angle perspective of the confined space) and another camera feed may be outside of the confined space (e.g., angled toward the ingress or egress to the confined space). Worker status (606) may be displayed above the camera feeds. The worker status indicates the number of workers or humans inside the confined space. Further, the worker status may include personal protective equipment readings of wearable monitoring equipment of the workers. Gas sensor indicators (608) show the gas measurement values of various gases in the confined space. The gas sensor indicators (608) may be the measurement values acquired by the gas sensors in the point monitor case. In one or more embodiments, the worker status (606) and the gas sensor indicators (608) are color coded based on the corresponding values. For example, if the worker status indicates too many workers, that a reading from a personal protective equipment does not satisfy a safety threshold, or that a piece of equipment is faulty, one or more of the worker status may be set to a red indicator whereas normal operation may be yellow or green. Similarly, if a gas sensor indicator (608) shows that the corresponding gas measurement value does not satisfy a safety threshold, the gas sensor indicator may be red. If the gas sensor indicator has a measurement value satisfying the safety threshold, the gas sensor indicator may be yellow or green.

Test button (610) is a user interface widget to initiate a test of one or more components of the confined space monitoring system. The test button may be color coded based on whether a test is due. For example, a red test button indicates that a test should be performed immediately. In one or more embodiments, the test button does not switch to indicate no test is needed until after the performance of the test is validated. As such, a user cannot change the button without performing the test in one or more embodiments.

Control buttons (e.g., control button A (614), control button B (616)) are user interface widgets to control the corresponding camera from which the corresponding camera feed (e.g., camera feed A (602), camera feed B (604)) is obtained. In one or more embodiments, the control buttons are small icons. Specifically, the control button may be used to remotely initiate a pan, tilt, and zoom setting of the camera and, thus, adjust the corresponding camera feed.

Although not shown, the user interface further shows the required personal protective equipment (PPE) for the confined space. The required PPE is shown in the local user interface as icons that are specific to the type of PPE (e.g., safety glasses, hard hat, ear protection, goggles, etc.). In other words, an icon showing goggles means that workers in the area must be wearing goggles. Thus, a user viewing the camera feeds in the local user interface may see the goggle icon and check that the workers shown in the camera feed are wearing goggles. The one or more PPE icons may be to the right of the camera feed aligned with the control buttons and test buttons. As another example, the one or more PPE icons may be below the camera feeds aligned with the control buttons and test buttons.

Figures 7B, 7C:
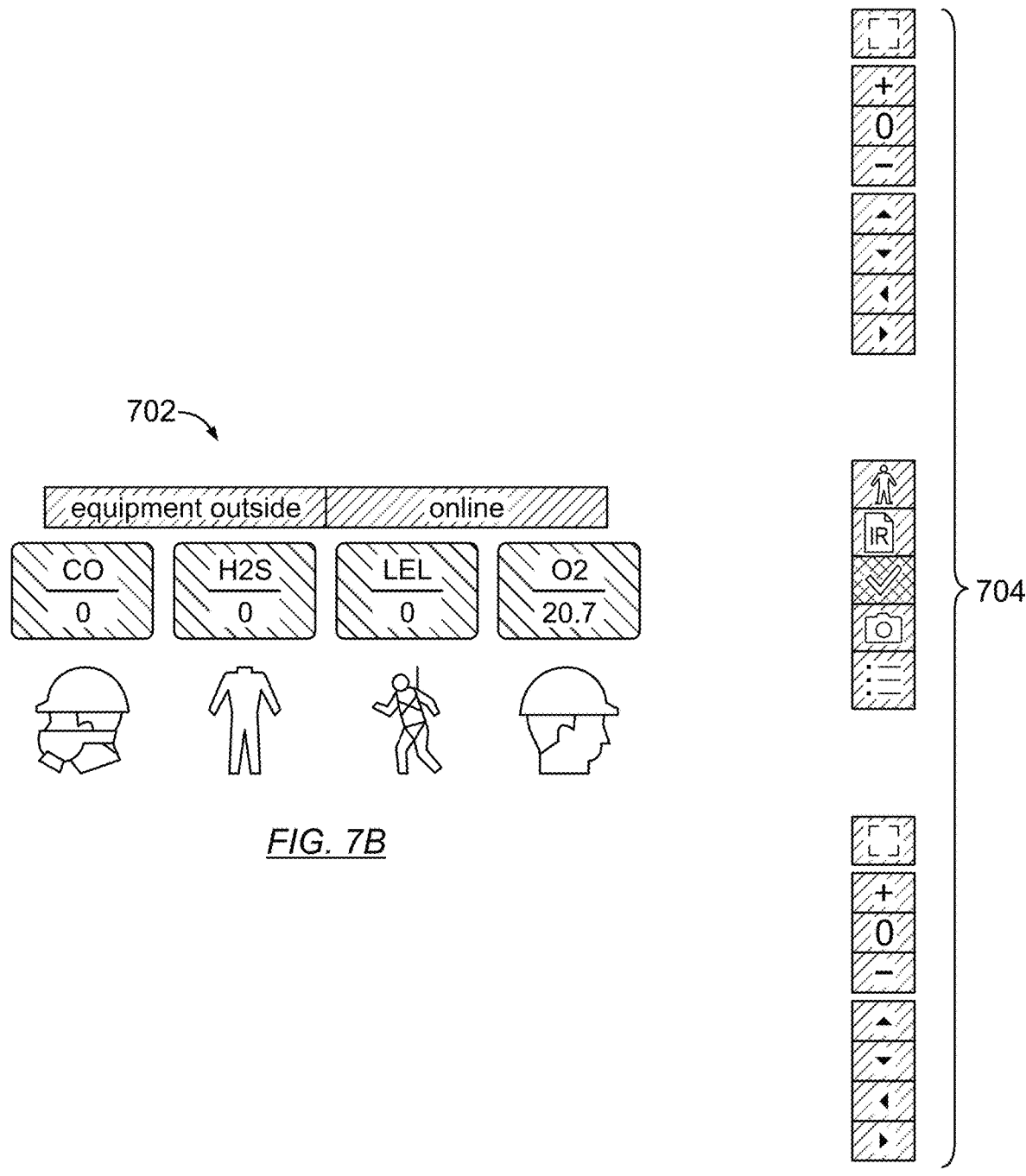

Although FIG. 6 shows the user interface (600) for a single confined space, the user interface may show multiple confined spaces. An example of the user interface (700) for a set of confined spaces is shown in FIG. 7A. As shown in FIG. 7A, the confined spaces are in a tile view, whereby each confined space is in an individual tile. The tile includes two camera feeds in stacked orientation, two rows (702) beneath the camera feed, and the set of buttons to the right of the two camera feeds. An expanded version of the two rows (702) are shown in FIG. 7B. Specifically, FIG. 7B shows the expansion of the rows underneath the second column bottom row confined space. The remaining confined spaces have a similar interface as shown in FIG. 7B. Accordingly, the example shown in FIG. 7 has ten tiles showing ten confined spaces. Beneath the camera feed is two rows of information (702). The top row of the two rows (702) are gas sensor indicators that include values for carbon monoxide (CO), H25, lower explosive limit (LEL) (i.e., a measure of an amount of combustible gas in the air), and oxygen (O2). Below the gas sensor indicators is a second row having the PPE icons showing the safety equipment workers must wear when being within the confined space. The control buttons and test button (704) are to the right of each confined space camera feeds and allow the user to control various monitoring devices in the confined space system. A test button, when triggered, initiates a test the connection and devices of the confined space monitoring system. An expanded view of the control buttons and test button (704) is shown in FIG. 7C. Specifically, FIG. 7C shows the expansion of the control buttons and test button to the right of the confined space in the top row and second to the last column. The remaining confined spaces have a similar interface as shown in FIG. 7C. The user interface of FIG. 7A is displayed on the primary display device and allows the user a single whole view of the status of the various confined spaces being monitored. As described above, the user interface of FIG. 7A is driven by the software components of FIG. 5.

While FIGS. 1-7C show a configuration of components, other configurations may be used without departing from the scope of the invention. For example, various components may be combined to create a single component. As another example, the functionality performed by a single component may be performed by two or more components.

Figure 8:
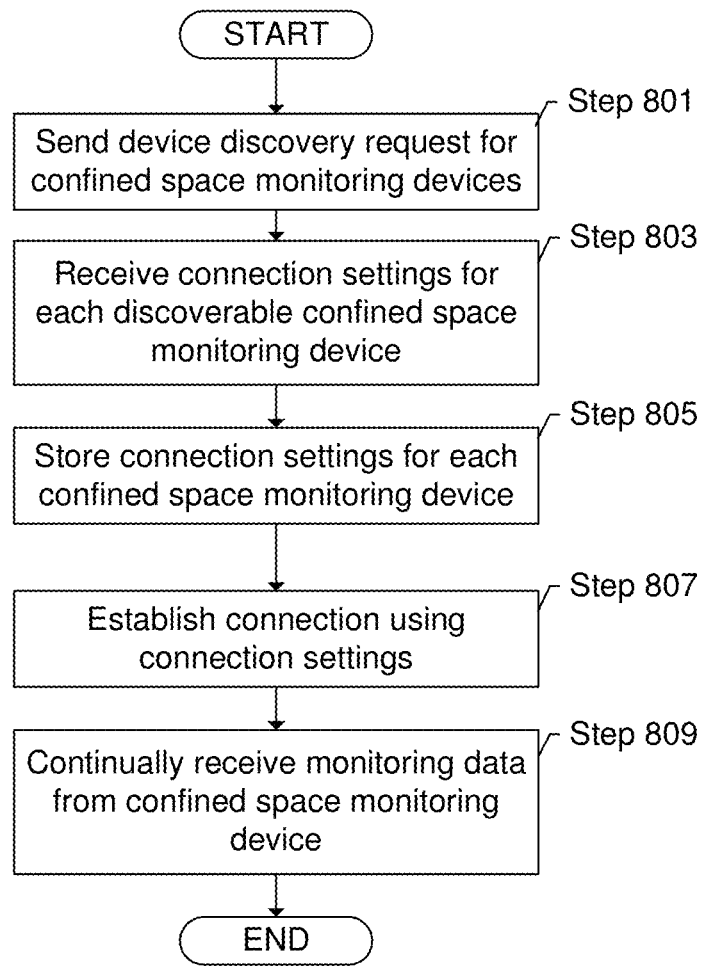
FIGS. 8 and 9 show flowcharts in accordance with one or more embodiments of the invention.
Figure 9:
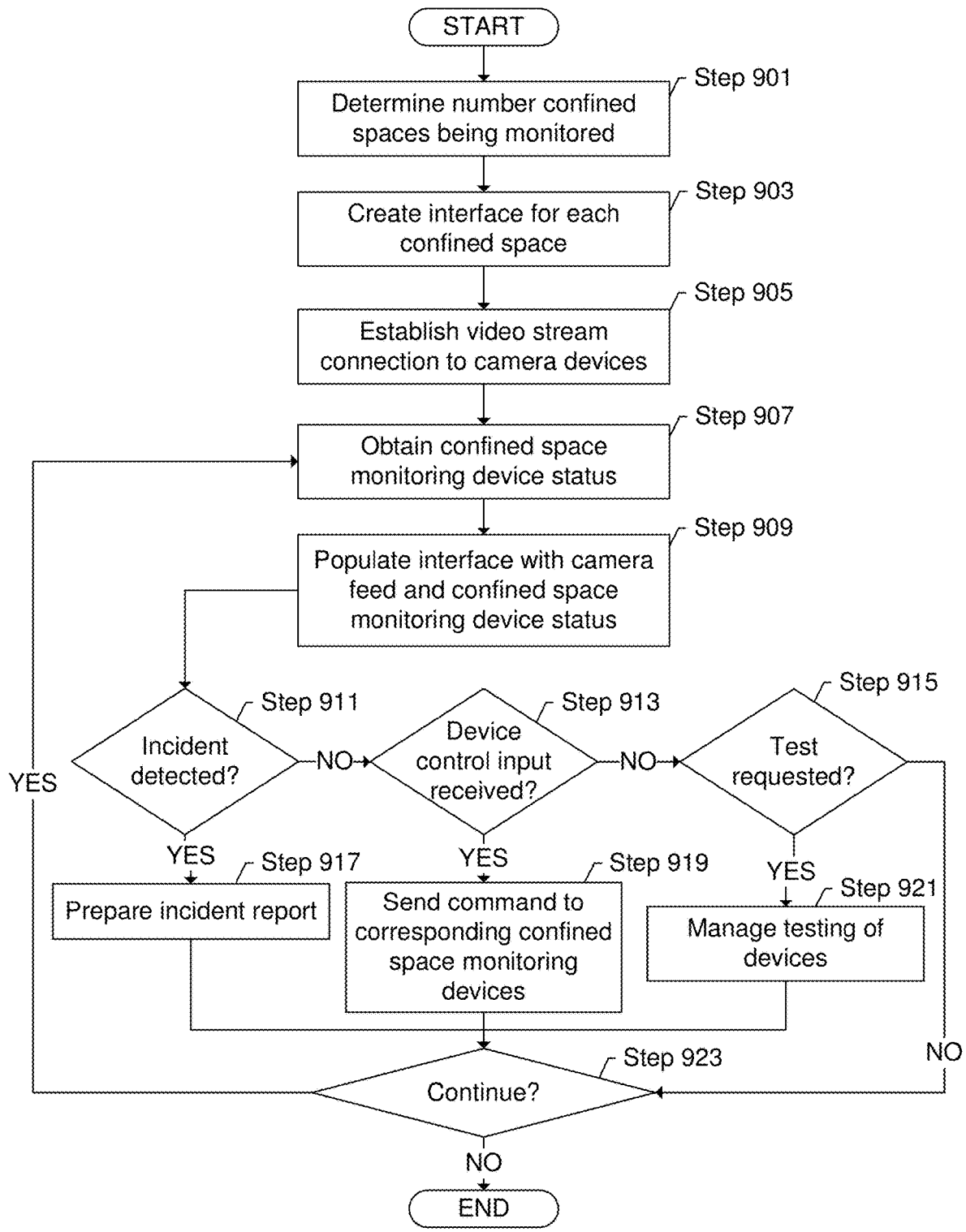

FIGS. 8 and 9 show flowcharts in accordance with one or more embodiments. While the various steps in these flowchart are presented and described sequentially, one of ordinary skill will appreciate that some or all of the steps may be executed in different orders, may be combined or omitted, and some or all of the steps may be executed in parallel. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention.

FIG. 8 shows a flowchart for acquiring information from monitoring devices in the confined space system. In Step 801, a device discovery request is sent to the confined space monitoring devices. At the confined space, one or more of the monitoring devices are connected to ports of the point monitoring case. Some of the devices, such as the cameras, may establish a wireless connection with the point monitor case. A ping command may be transmitted between the hub and the point monitor cases and the monitoring devices. Similarly, the centralized monitoring application may be configured with the IP address of the hub and may issue a request for the point monitoring cases. The hub may respond with IP addresses of the point monitoring cases. The centralized monitoring application may further ping the monitoring devices based on the IP address of the hub and point monitor case to obtain the addresses of the monitoring devices.

In Step 803, connection settings are received for each discoverable confined space monitoring device. The connection settings may indicate how to connect to the various monitoring devices and point monitoring cases. Namely, the connection settings, received in response to the ping command, establish the address and the protocols for connecting to the monitoring devices.

In Step 805, the connection settings are stored for each confined space monitoring device. In one or more embodiments, the connection settings are stored in the data repository, such as the database described above with reference FIG. 5.

In Step 807, a connection is established with each confined space monitoring device. Using the connection settings, the centralized monitoring application initiates a connection to receive the measurement values and video streams from the monitoring devices.

In Step 809, the monitoring data is continually received from each confined space monitoring device. The monitoring data is received via the point monitor case, through the hub and then to the centralized monitoring application.

Below is a discussion of a technique for acquiring monitoring data from a gas detector, a badge reader, and cameras in accordance with one or more embodiments. The subnet assigned to the gas detector indicates the type of gas detector, and accordingly the connection settings for the gas detector.

For each modbus gas detector, a transport control protocol (TCP) connection to is established with the modbus gas detector. In other words, the connection is with a device controller on the gas detector. For each connection, an application method may read a register from the modbus controller and return an array holding the values of the register. The received values in the array are processed to create a measurement object, which are written to a database. The measurement values are processed by the gas detector service and the graph renderer.

For a PLC gas detector, the connection is established to read values and save the values to the database when a ping to the plc has succeeded. A TCP or serial connection may be established with the PLC gas detector. As part of establishing the connection, the gas type and the unit of measurement may be determined. Through the connection, measurement values are acquired and written to a buffer. The buffer is consumed by a database and by the gas detector service and the graph renderer.

Cameras may be discovered using a ping command. When a camera is discovered, the camera is added to the camera set. A connection is established to the camera, and the camera feed is obtained through the connection. As the camera feed is received, the camera feed is recorded and stored with timestamp information.

For the badge reader, a communication bus proxy may be created in the communication bus. Using the communication bus proxy and using a connection to a database of the badge reader, the available confined space areas monitored by the badge reader are determined. Further, count data and the identifiers of people inside the confined space are obtained.

FIG. 9 shows a flowchart for a user interface in accordance with one or more embodiments. In Step 901, the number of confined spaces being monitored is determined. The user interface generation software components may query the database to identify the number of confined spaces. The database may be populated with information about the confined spaces from the hub(s) connected to the centralized monitoring station cabinet.

In Step 903, an interface for each confined space is created. Namely, a portion of the local interface is allocated to each confined space being monitored.

In Step 905, a video stream connection is established to the camera devices. For each confined space being monitored, the connection settings for the one or more cameras in the confined space system are obtained. The cameras are configured to transmit the camera feed to the centralized monitoring station cabinet. The user interface generation software components relate the camera feed to an assigned portion of the local interface for the confined space.

Further, confined space monitoring device status is obtained in Step 907. For each monitoring device, the confined space monitoring device status includes any measurement values, readings, and whether faults exist. The status may be transmitted continually or periodically. In one or more embodiments, the status is transmitted to the centralized monitoring application automatically by the point monitor case that reads the device status from a register on each device. The point monitor case may transmit the device status as a data stream to the centralized monitoring application.

In Step 909, the user interface is populated with the camera feed and the confined space monitoring device status. In other words, the camera feed and the confined space monitoring device status is presented in the user interface.

Using the user interface, the user may trigger several actions based on a review of the camera fee and the confined space monitoring device status. In Step 911, a determination is made whether an incident is detected. An incident is the occurrence of an unplanned event and has the ability to cause bodily or physical damage. Incidents may be automatically detected or detected by a human operator. For example, explosions, gas readings indicating a toxic environment, too many people in the confined space may be detected by the confined space monitoring system. A person getting injured, appearing sick, or unsafe conditions may be detected by a human operator. In such a scenario, if an incident is detected, the user interface guides the user to prepare an incident report in Step 917. Specifically, the confined space monitoring application gathers the data surrounding the incident and interfaces with the user to generate the incident report.

As another example of using the user interface, the user may want to configure the confined space monitoring devices. In Step 913, a determination is made whether device control input is received. For example, a user may select the control buttons in the user interface to trigger configuring the confined space monitoring application. If device control input is received, a command is transmitted to the corresponding confined space monitoring devices in Step 919. The control buttons are related to an underlying monitoring device. Using the connection settings for the monitoring device, a command is transmitted via the hub and the point monitor case to the controller located on the monitoring device. The controller subsequently adjusts the configuration of the monitoring device. For example, for a camera, a zoom command may be transmitted to the controller of the camera in accordance with the predefined protocol of the camera. The controller may adjust the amount of zoom according to the zoom command.

In Step 915, a determination is made whether a test is requested. For example, the user interface may display a test button indicating that a daily test of the system is due. As another example, a user may initiate a test in response to an upgrade or detecting a fault in the confined space monitoring system. If a test is requested, then the testing of the devices is managed in Step 921. Specifically, the confined space monitoring application guides the user through testing each connection and each device of the confined space monitoring system.

In Step 923, a determination is made as to whether to continue. The confined space may be continually monitored until a worker is not present or the hazards are properly managed.

Although FIGS. 7-9 are described with respect to the local interface, the same or similar functionality is available on the web interface in accordance with one or more embodiments. Further, the same or similar functionality exists on the application interface of the hub and the point monitor case for connected devices in accordance with one or more embodiments.

The following Figures show examples in accordance with one or more embodiments. The examples are for explanatory purposes only and not intended to limit the scope of the invention unless expressly required by the claims.

Figure 10D:
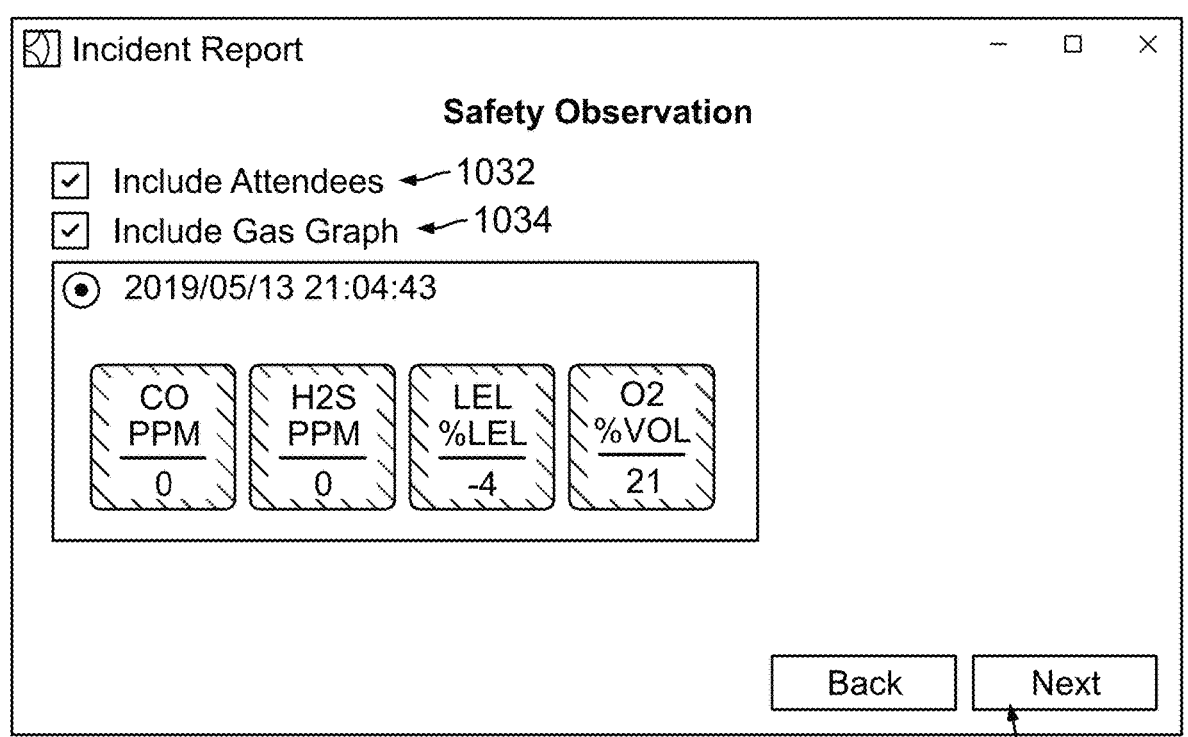

FIGS. 10A, 10B, 10C, 10D, 10E, and 10F show an example interface for an incident report in accordance with one or more embodiments of the invention. As shown in FIGS. 10A-10F, the confined space monitoring application assists the user through the generation of the incident report through several guided screens. FIG. 10A shows the user interface (1000) for the user to provide contact information and start a safety operation. The user may indicate to whom the incident is reported (1002), the role of the user (1004), the nature of the incident (1006), and any involved party (1008). For the purposes of the example, consider the scenario that the incident is determining that a worker is in the confined space without the required protective gear of a helmet. Accordingly, the worker has not satisfied the safety protocols.

The user may next be guided to FIG. 10B, where the user is able to list one or more reasons in fields (1012) of user interface (1010) that the user believe that the incident occurred. In the example, the user states the reasons as being because various properties of the helmet. When the user selects the next button (1014), the user is guided to FIG. 10C.

In FIG. 10C, the user interface (1020) includes fields (1022) for the user to select additional factors of the incident and fields (1024) to indicate the way in which the incident was detected, the actions advised and taken, timing of the incident, the result that occurs when the actions are taken. When the next button (1026) is selected, the user interface (1030) of FIG. 10D is shown.

Figure 10F:
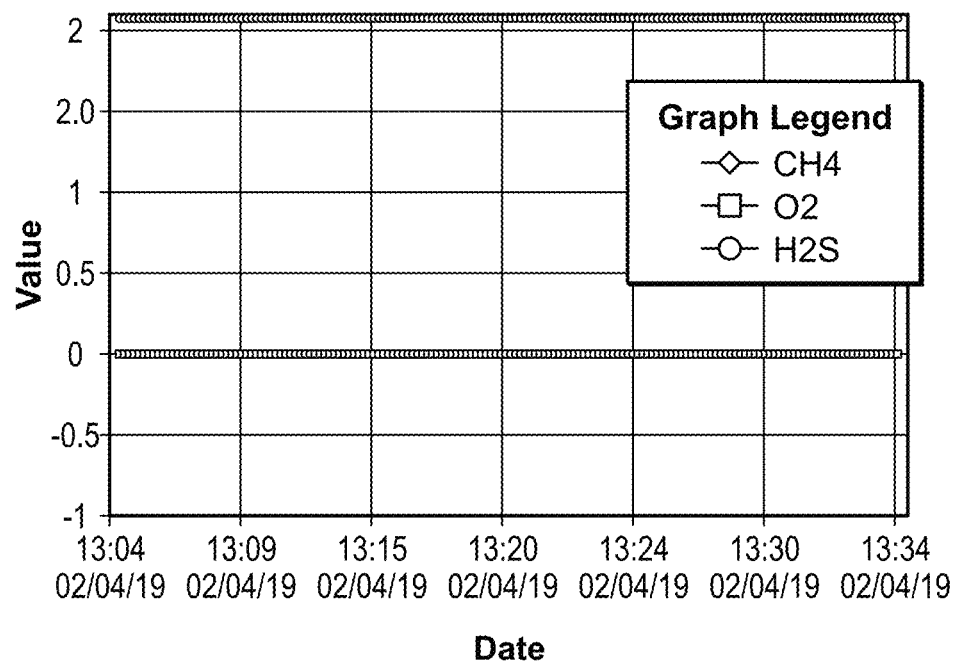

In the user interface (1030) of FIG. 10D, a user may select the monitoring data to include in the incident report. The monitoring data that the user may select in the example, may include list of attendees (1032) (i.e., workers at the confined space system) and a gas graph (1034) showing the gases that were present at the time. Notably, the user does not need to submit the measurement values or list the attendees because the information is acquired automatically from the database based on the timestamp of the incident and the time of the measurement values. When the save button (1036) is selected, the user interface (1040) shows the incident report, as shown in FIG. 10E and FIG. 10F.

As shown in FIG. 10E, the incident report is displayed in the interface (1040). FIG. 10F shows the continued user interface (1040) with incident report from FIG. 10E. The incident report shows information submitted by the user as well as information acquired by the centralized monitoring application from the database. For example, as shown in FIG. 10F, the incident report may include stills from the camera feed, a list of names of workers present, which companies are represented, and when the workers entered the confined space, a gas graph, etc. The incident report is automatically formatted into a defined style. Thus, if a worker does not wear their helmet again or if an accident happens, the recording of the incident may prove that the worker was warned.

Figure 11A:
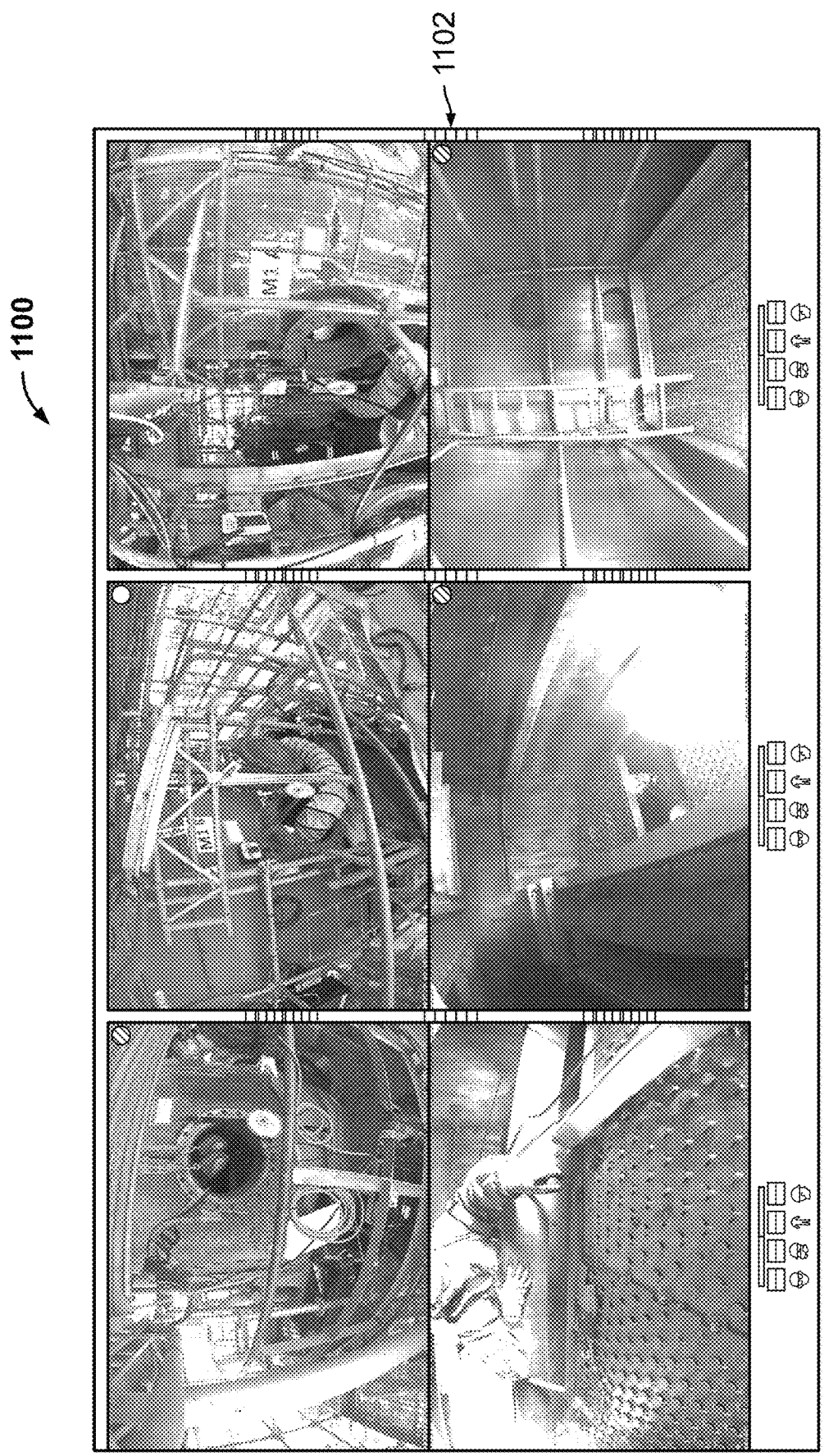

As described above, the user interface also is configured to guide the user through performing a system test. FIGS. 11A, 11B, 11C, 11D, 11E, 11F, 11G, and 11H show an example interface for a system check in accordance with one or more embodiments of the invention. FIG. 11A shows an example user interface (1100) on the primary display device with a system test button (1102) indicating that a system test is due. When the user selects the system test button (1102), the user is guided through performing a system test starting with FIG. 11B.112

Figure 11B:
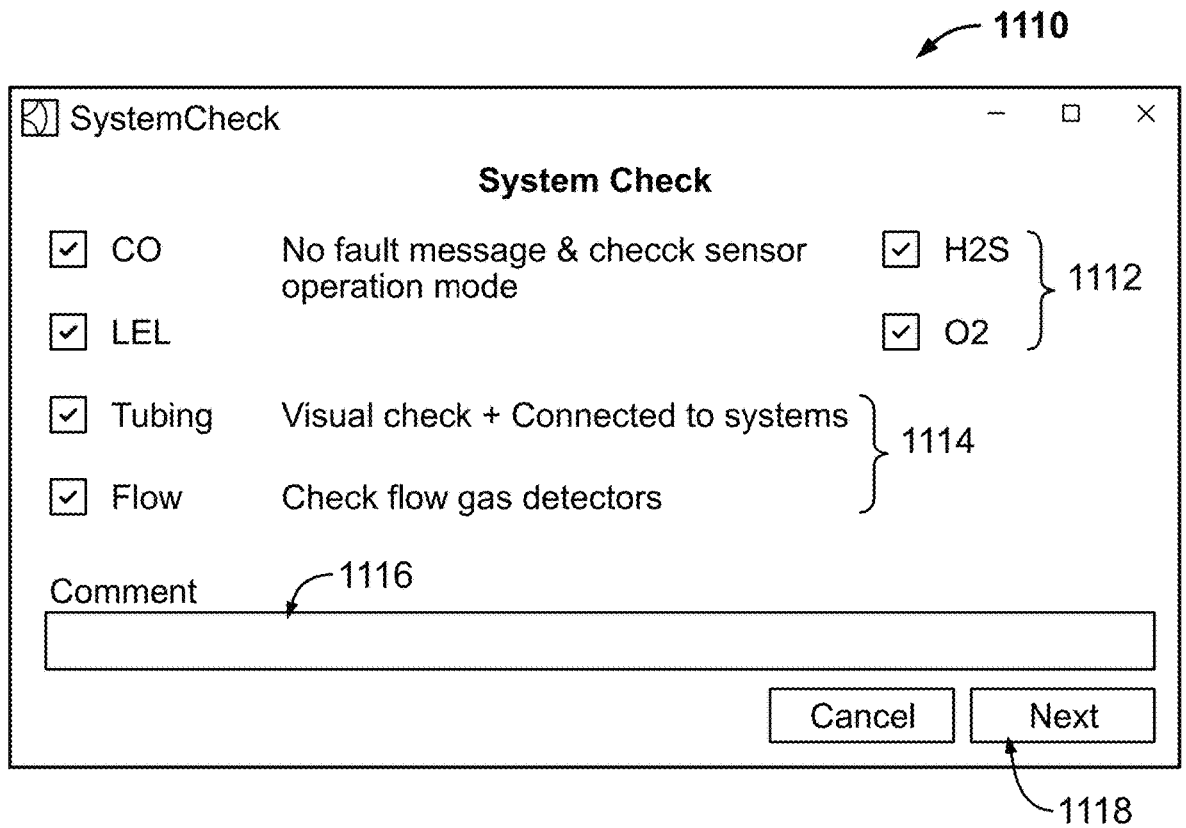

FIG. 11B shows the user interface (1110) when the user selects the system test button of the user interface. As shown in FIG. 11B, the user interface (1110) initiates performing a gas detector check. The gas detector check includes checking the various gas detector sensors (1112) as well as the tubing (1114) to the gas detector sensors. The user may have a worker manually perform the check. As another example, the gas detectors may include functionality to perform self-testing. The user may also add comments in field (1116) regarding the gas detector check. When the user selects next box (1118), the user may be guided to user interface (1120) shown in FIG. 11C.

Figure 11C:
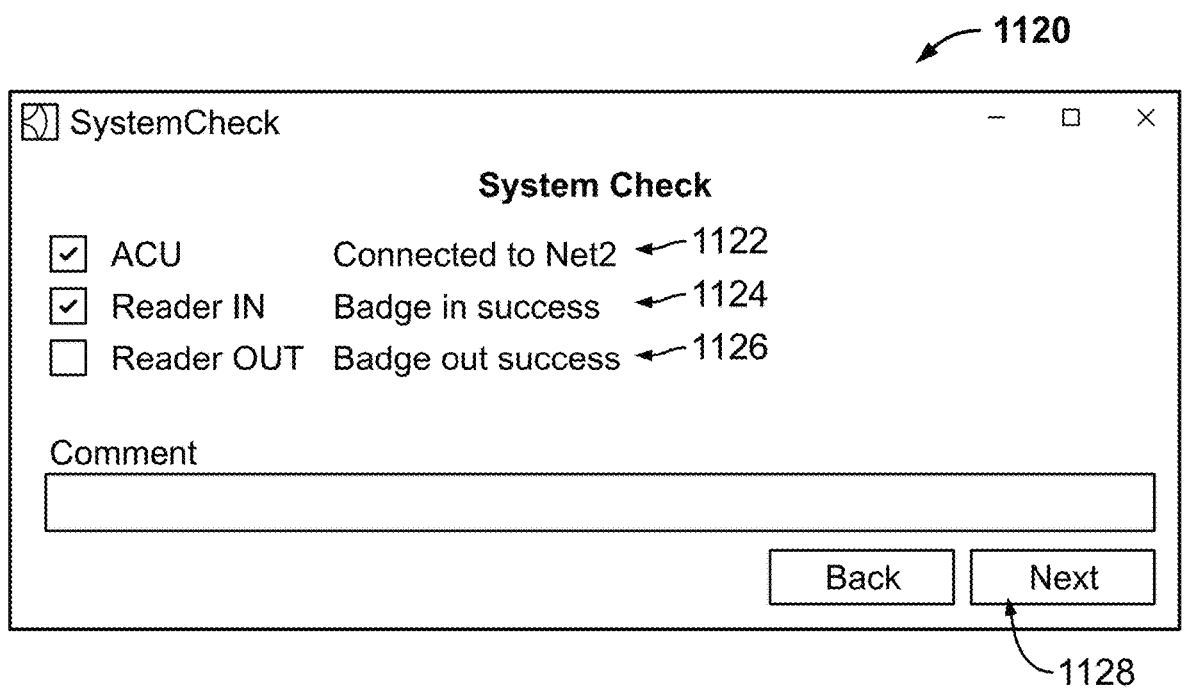

FIG. 11C shows a user interface (1120) to perform a badge reader check of badge readers at the confined space. The user may confirm that the badge reader (1122) is connected and a worker is able to badge in on ingress (1124) and badge out on egress (1126) of the confined space. On selection of the next button (1128), the user interface (1130) of FIG. 11D is shown.

Figure 11D:
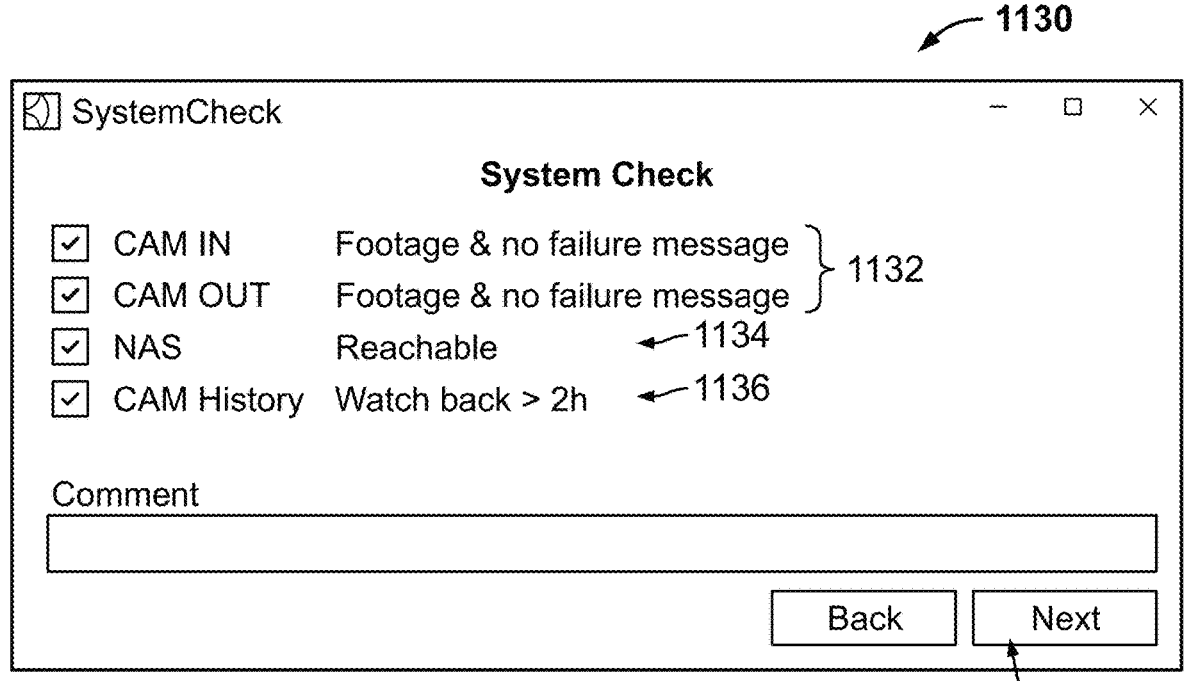

In FIG. 11D, the user interface (1130) is presented to perform a camera check of cameras at the confined space. The camera check includes checking both cameras (e.g., that camera feeds exist and a failure message is not received) (1132), that a NAS drive is connected for the cameras (1134), and that camera history (1136) is being saved for a specified time period (e.g., two hours). When the next button (1138) is selected, the user interface (1140) of FIG. 11E is shown.

Figure 11E:
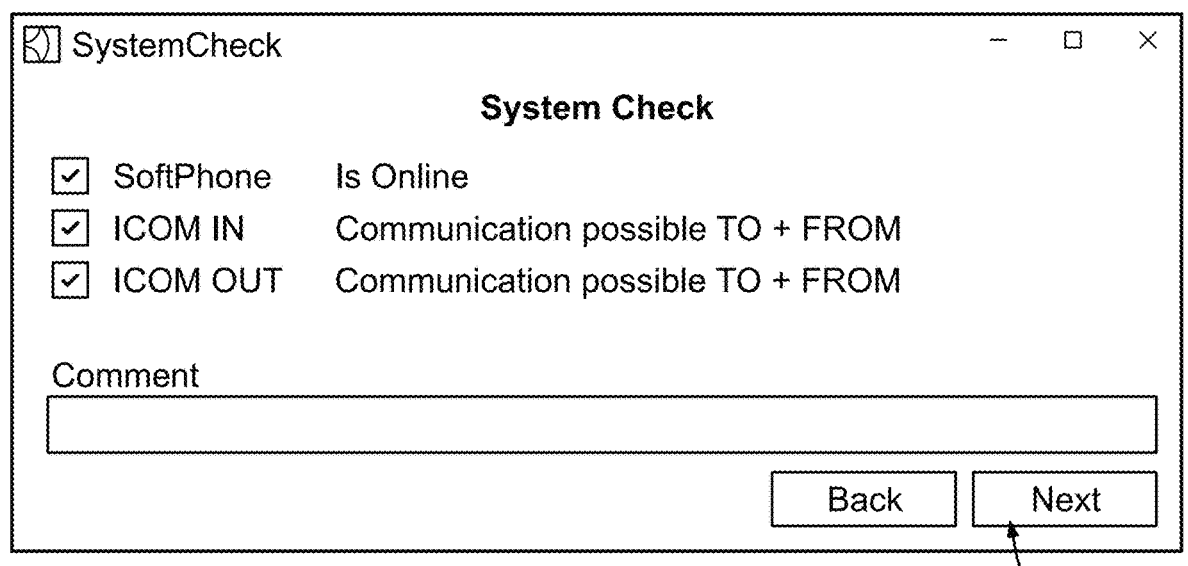

In FIG. 11E, the user interface (1140) guides the user through checking the intercom device. Specifically, the communications are tested. When the next button (1142) is selected, the user interface (1150) of FIG. 11F is displayed.

Figure 11F:
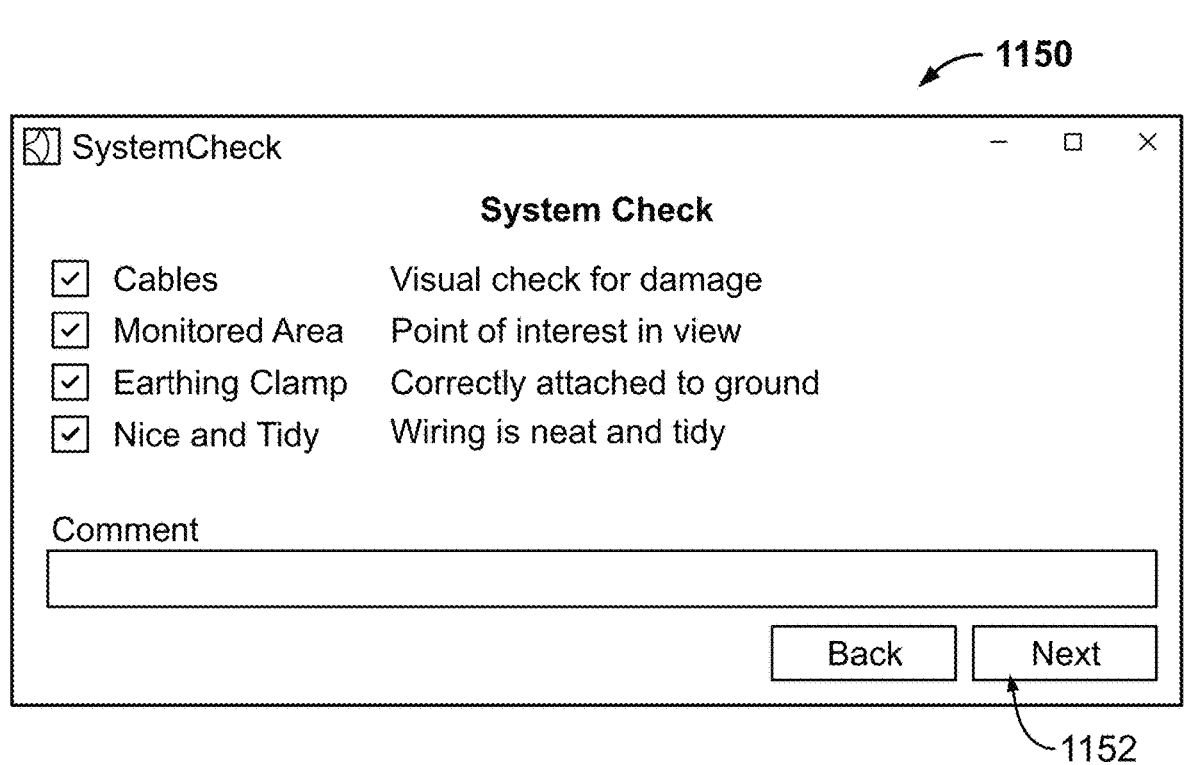

In FIG. 11F, the user interface (1150) guides the user through checking the overall installation. Namely, the overall installation includes checking cables for damage, that the wiring is neat, monitored area is in view of the point monitoring case, that the system is grounded. When the save button (1152) is selected, the user interface (1160) shows the system check report shown in FIG. 11G.

Figure 11G:
Figure 11G:
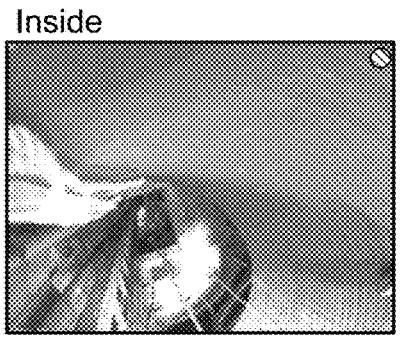
Figure 11G:
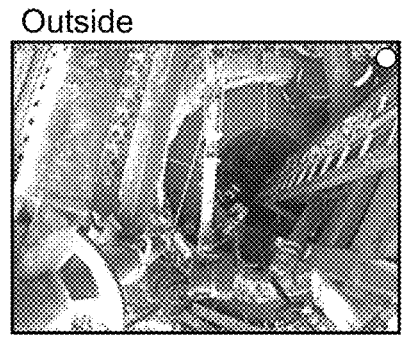

As shown in FIG. 11G, the system check report user interface (1160) lists who performed the system test, what was tested, and the results of the test. The system check report user interface continues on FIG. 11H. Specifically, FIG. 11H shows a second page of the user interface (1162) of the system check report.

Figure 12A:
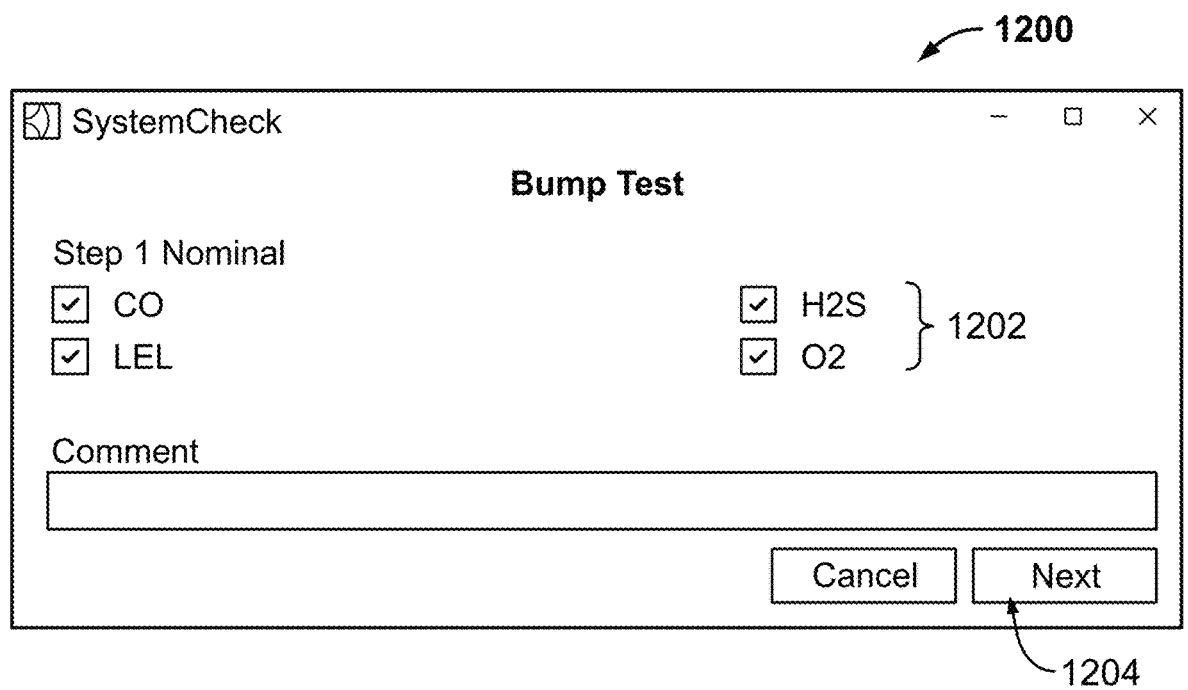
FIGS. 12A, 12B, 12C, 12D, and 12E show an example interface for system check bump test in accordance with one or more embodiments of the invention.
Figure 12B:
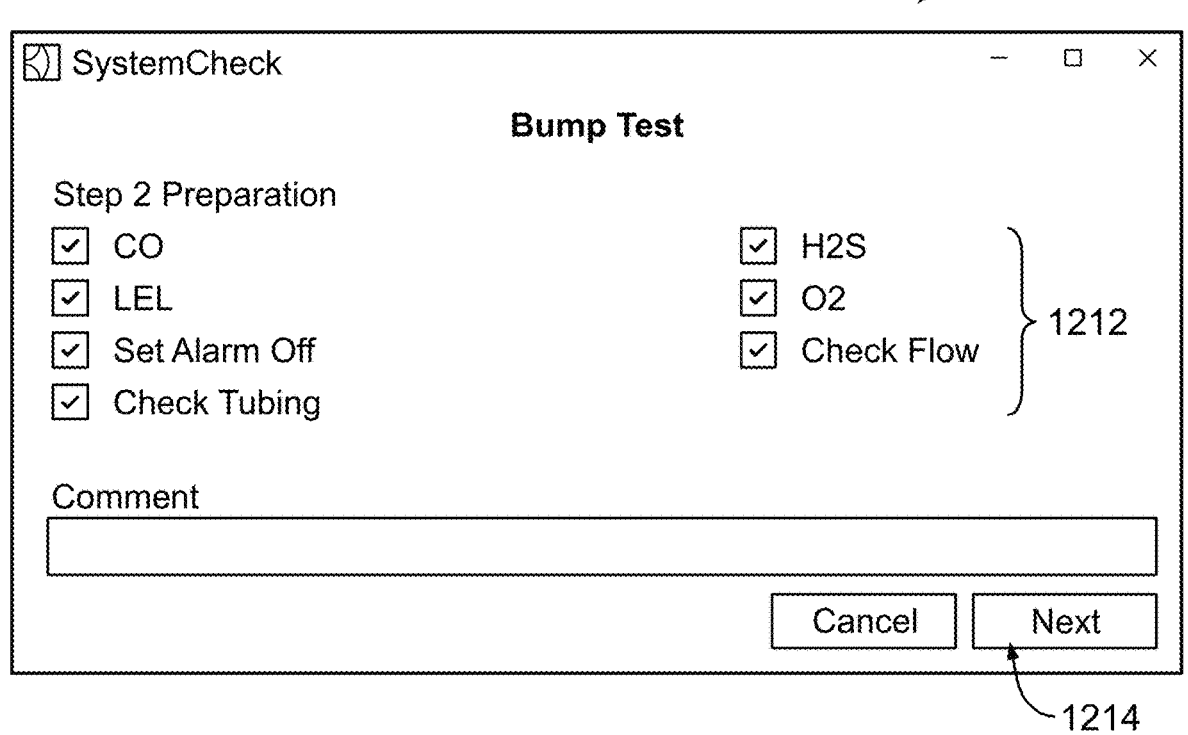

FIGS. 12A, 12B, 12C, 12D, and 12E show an example interface for system check bump test in accordance with one or more embodiments of the invention. The bump test is the process that verifies that the performance of the gas detector sensors and that the sensors are responding to target gases. The user interface guides the user through performing the bump test. Turning to FIG. 12A, the user interface (1200) lists the various aspects to checking a nominal set of operations of the bump test. The nominal testing is an initial acquisition of the gas readings. The user may select various fields (1202) to define which gas detectors are tested. When the next button (1204) is selected, the user interface (1210) shown in FIG. 12B is displayed.

The user interface (1210) in FIG. 12B guides the user through a preparation phase of the bump test. In the preparation phase, visual checks are performed of the gas sensors, tubing, and the alarm is tested. Once each item is complete, the user selects the corresponding field (1212). When the next button (1214) is selected, the user interface (1220) shown in FIG. 12C is displayed.

Figure 12C:
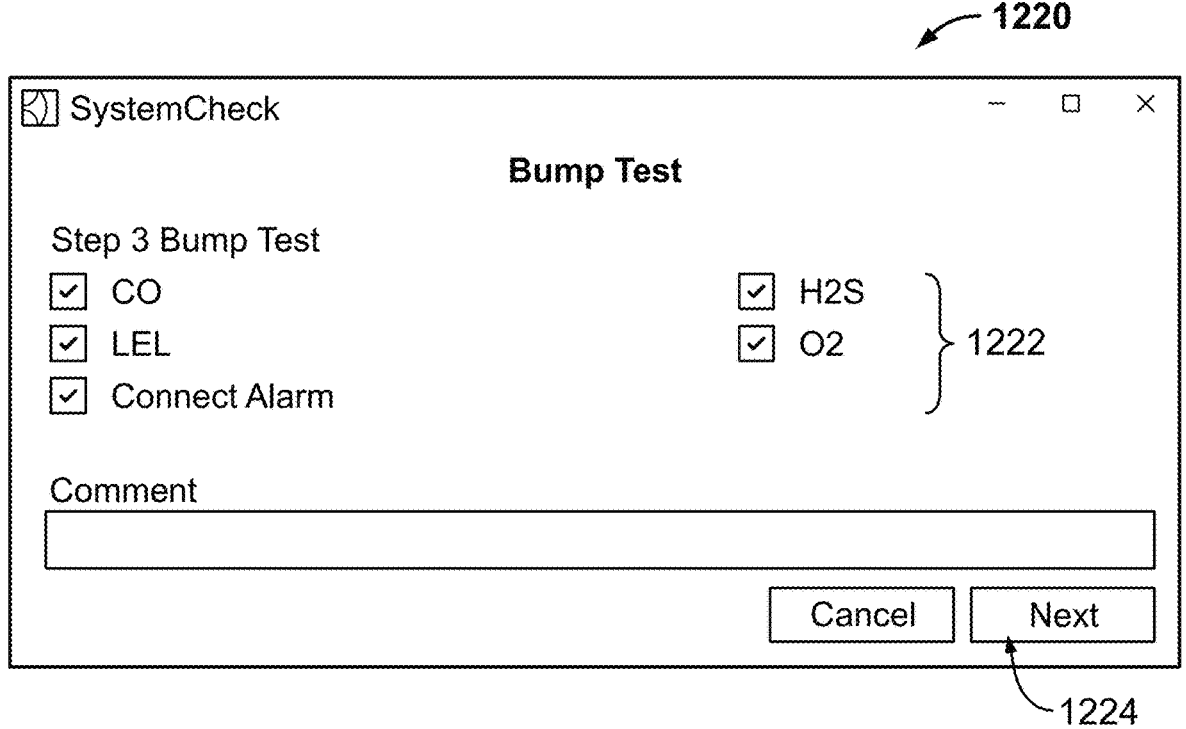

The user interface (1220) in FIG. 12C guides the user through performance phase of the bump test. During the bump test, the gas detectors are tested. When the testing is complete, the user checks the corresponding field (1222). When the next button (1224) is selected, the user interface (1230) shown in FIG. 12D is displayed.

Figure 12D:
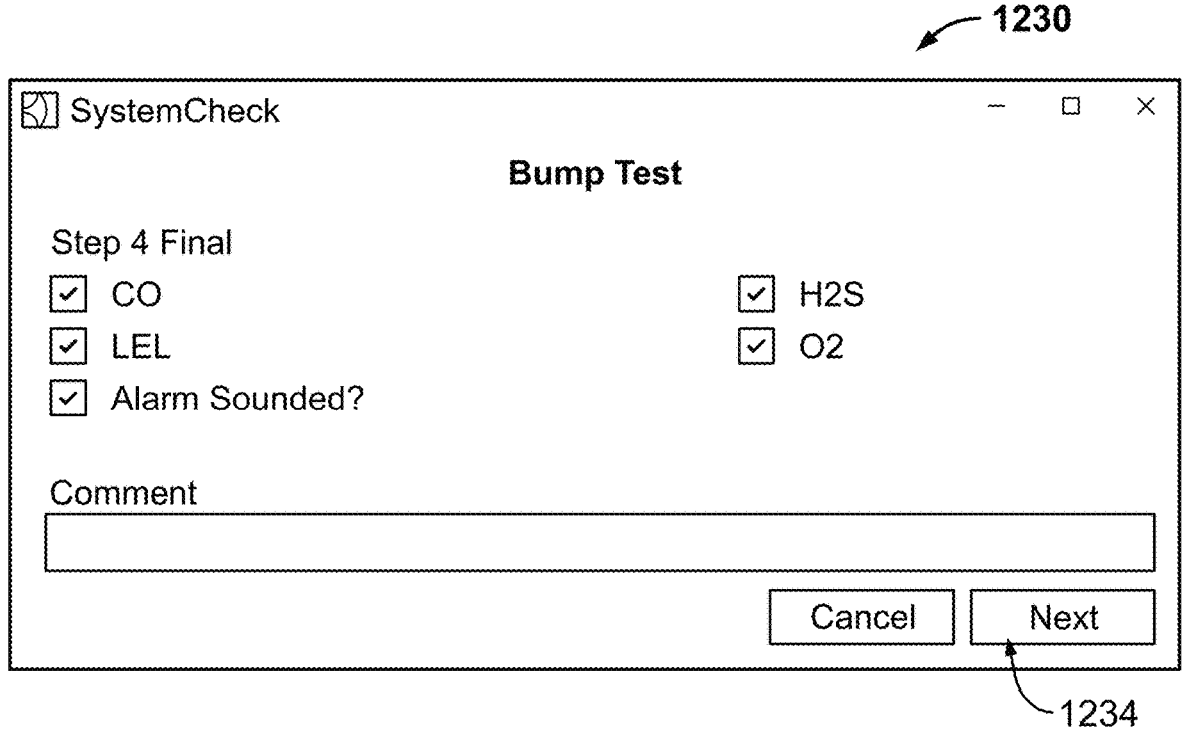
Figure 12E:
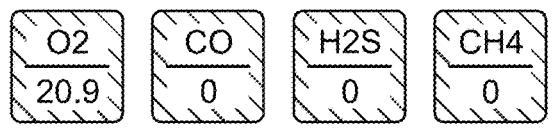
Figure 12E:
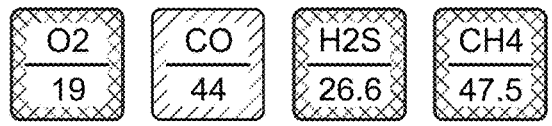
Figure 12E:
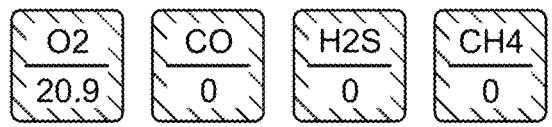

The user interface (1230) in FIG. 12D guides the user through a final check of the bump test. The final check modifies the gases to confirm that gas detector functions. When the save button (1234) is selected, the user interface (1240) shown in FIG. 12D is displayed. FIG. 12D shows the user interface (1240) with the bump test report.

Figure 13A:
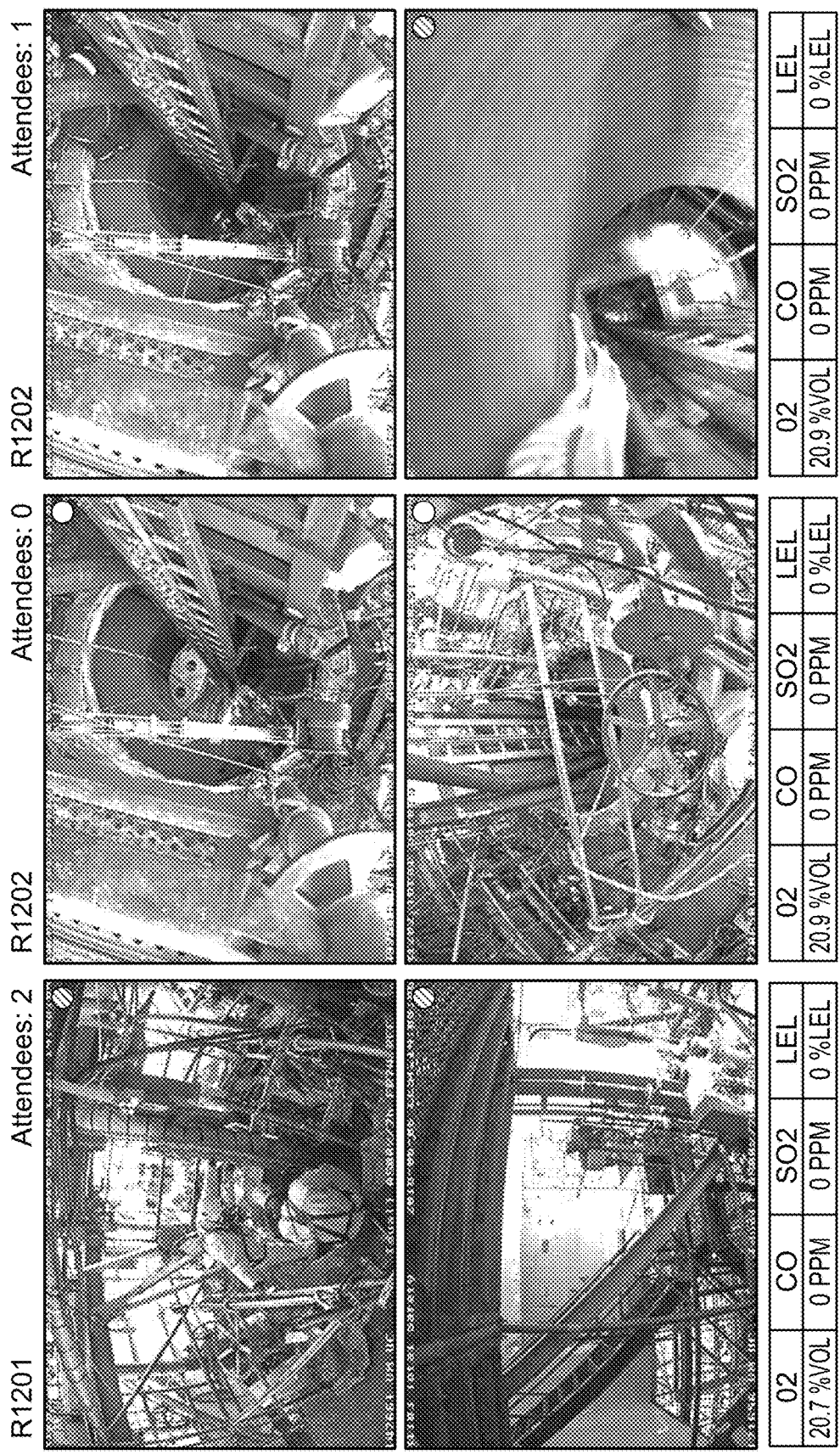

FIGS. 13A, 13B, 13C, 13D, 13E, 13F, and 13G show an example web interface in accordance with one or more embodiments of the invention. As shown in FIG. 13A the web interface (1302) may show much of the same information as the user interface shown above with reference to FIG. 7. Specifically, the web interface (1302) includes the camera views, gas readings, and information about the workers in the confined space. The web interface (1302) includes a customizable camera, gas detection, and attendee (i.e., worker) view, whereby a user may change a layout of the user interface.

Figure 13B:
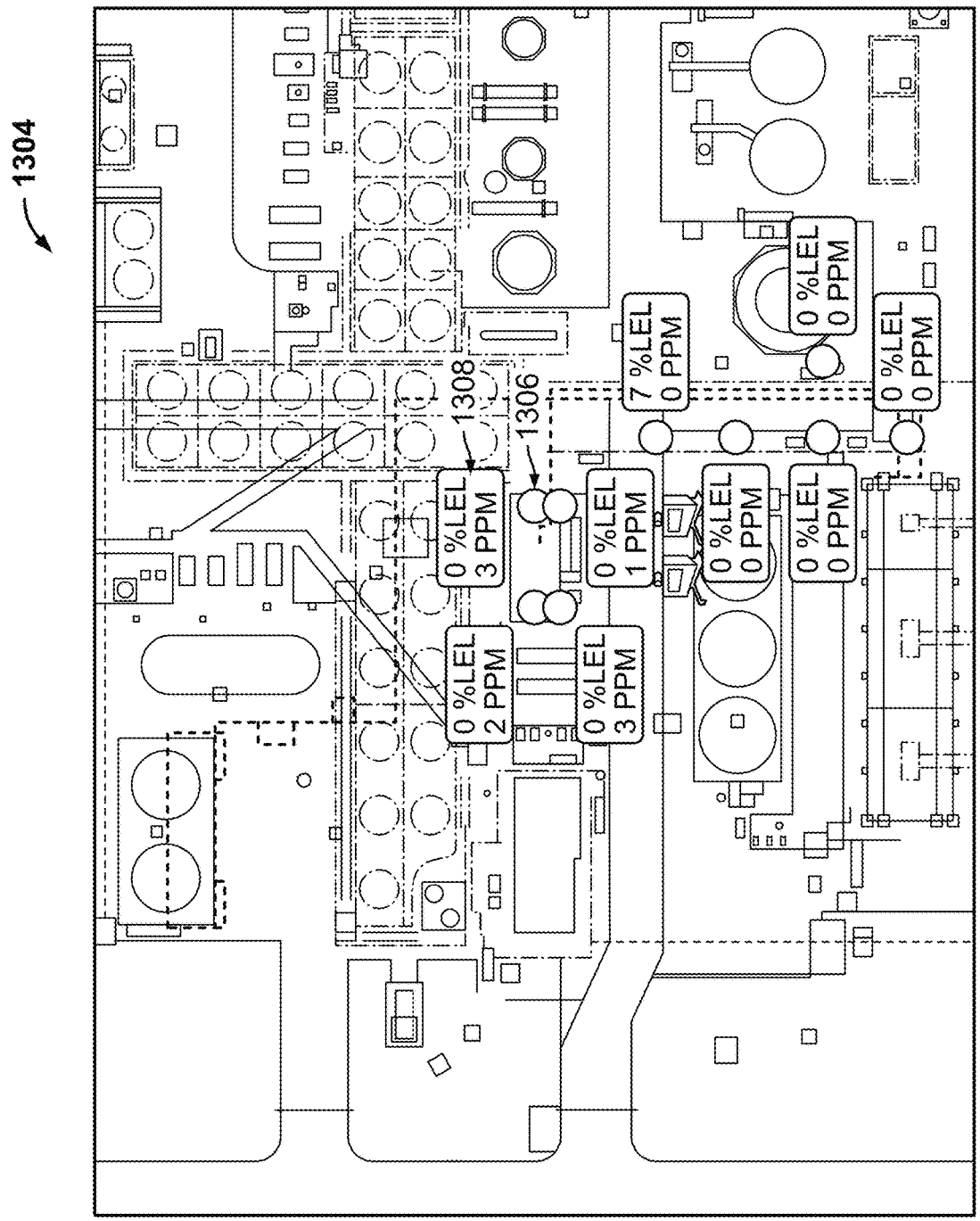

As shown in FIG. 13B, the web interface further includes a map view (1304) that shows a map of a locale having confined spaces (denoted with circles). As shown in FIG. A select set of parameters (1308), such as gas measurement values, number of people, etc. are shown on the map. Selecting a confined space system (e.g., a circle (1306) in the map view) results in showing the detailed parameters of a particular confined space. In one or more embodiments, when a confined space system is selected in the map view (1304), the detailed parameter view (1310) of FIG. 13C is displayed.

Figure 13C:
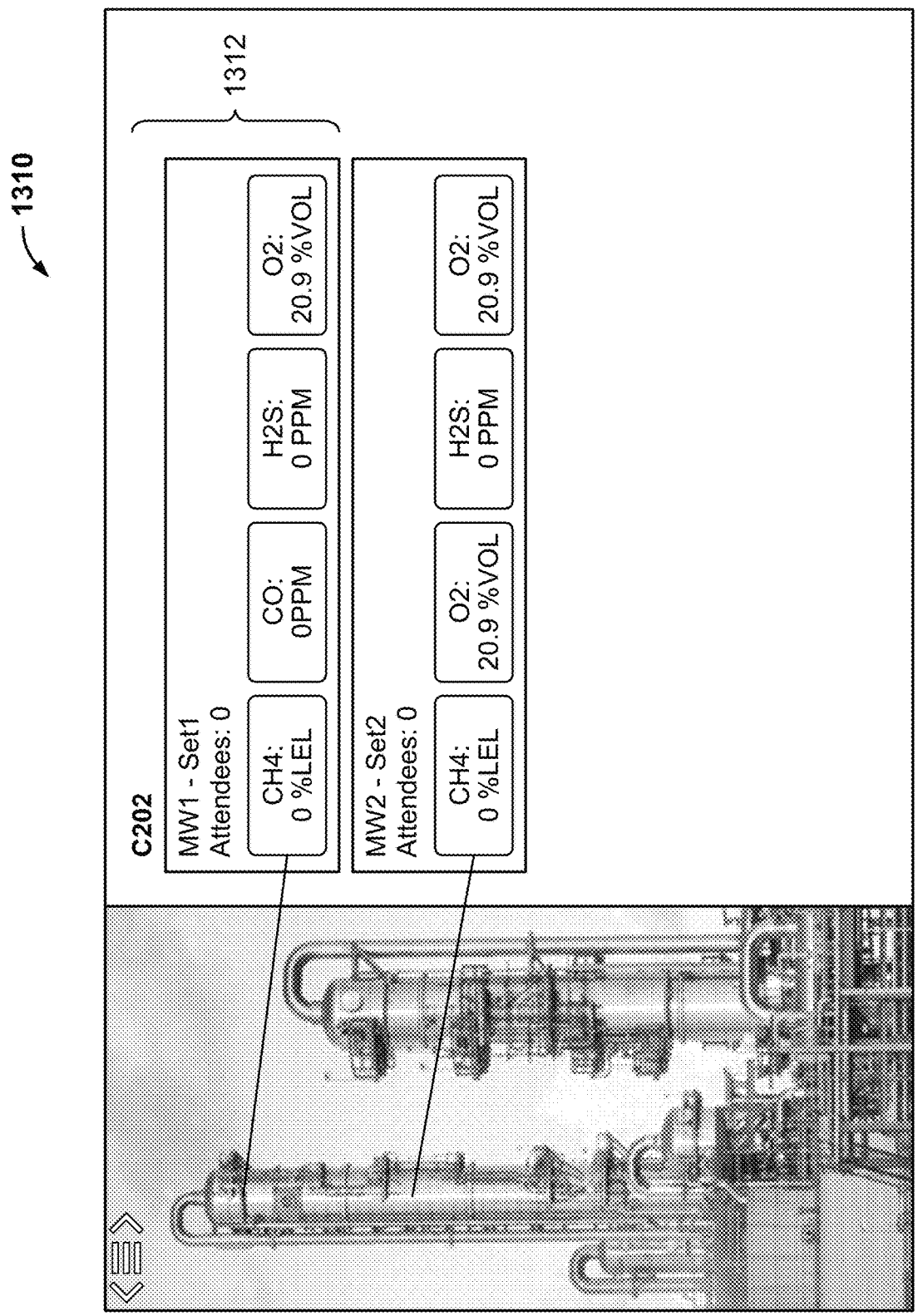
Figure 13D:
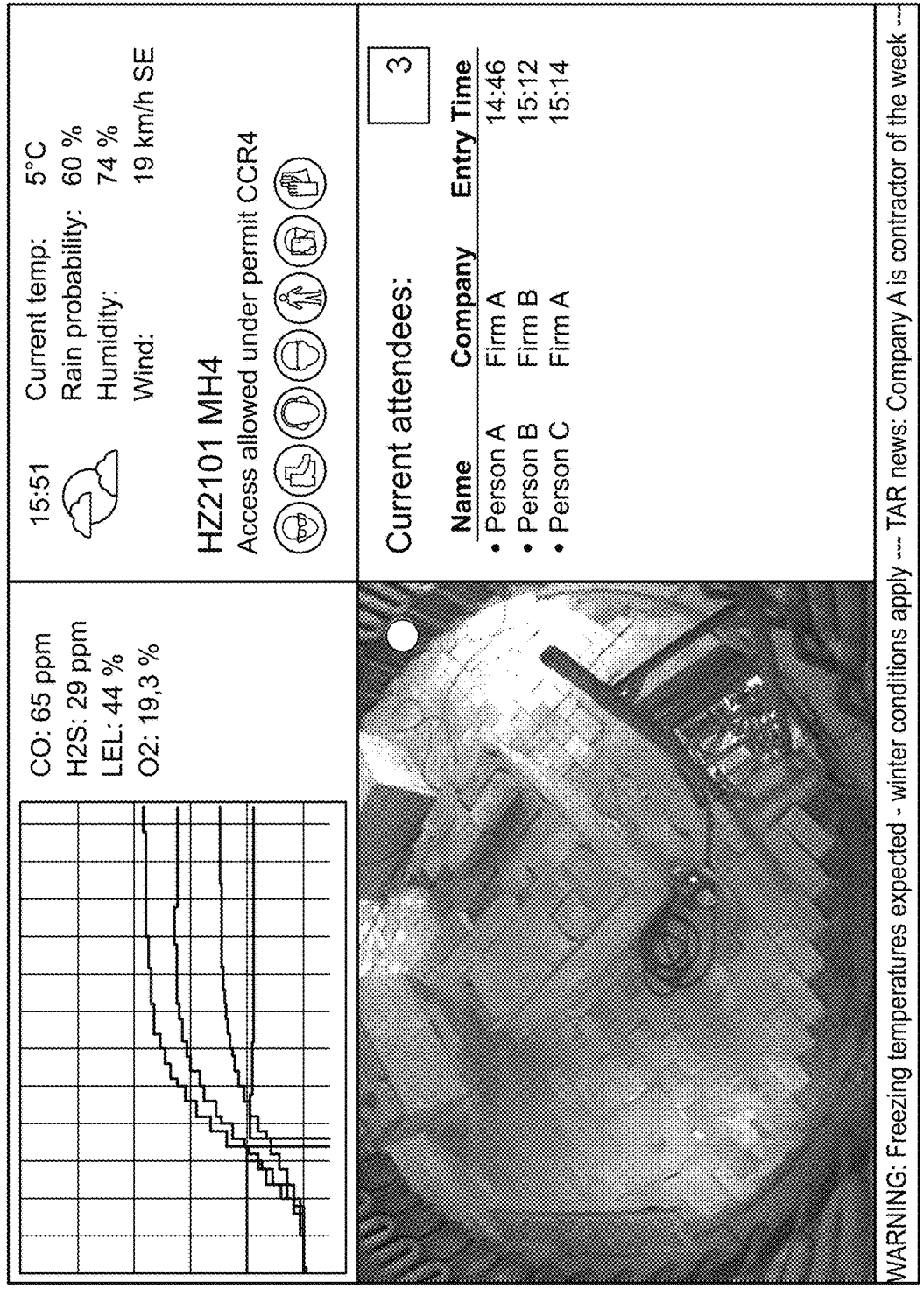

FIG. 13C shows a detailed parameter view (1310) when a confined space system is selected. The detailed parameter view (1310) is a customizable installation view with available parameters such as gas detection and attendees, split up per ingress to the confined space displayed. If an ingress is selected (e.g., ingress 1312), an ingress level view is displayed, such as the ingress level view (1320) of FIG. 13D. As shown in FIG. 13D, the ingress level view (1320) shows the details of the various parameters of the confined space including a camera feed.

Figure 13E:
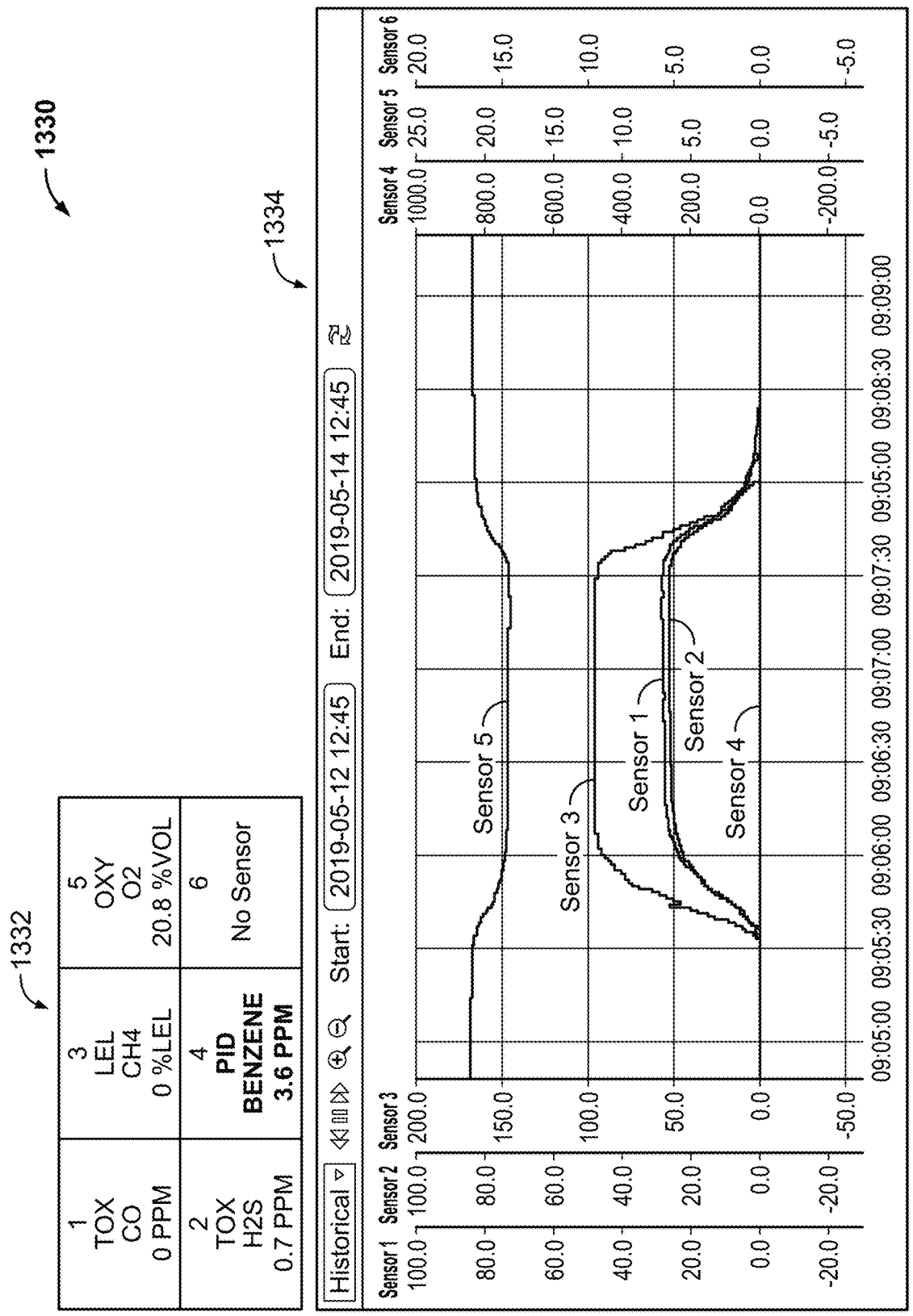

The web interface may further include a graph user interface (1330) as shown in FIG. 13E. As shown in FIG. 13E, the gas detection measurement values (1332) from a user defined start time to a user defined end time are shown in the web interface. Further, a graph (1334) of the gas measurement value are shown.

The web interface may further include a configuration interface (1340) as shown in FIG. 13F. In the configuration interface (1340), each gas detector is matched to a corresponding box (e.g., box (1342)). The values in the box are the configuration values for when to issue an alarm, and measurement values. Further, the user may specify the type of alarm and other settings using buttons (e.g., button (1344)). If the user selects settings button (1346), the user interface (1350) shown in FIG. 13G is displayed. As shown in FIG. 13G, the user interface (1350) displays various drop down boxes (e.g., drop down box (1352)) from which a user may modify a setting.

Although FIGS. 13A-13F are described with respect to the web interface, the local interface may include at least similar functionality as the web interface. For example, the local interface may also include a map view and the configuration interface or a form thereof.

Figure 14:
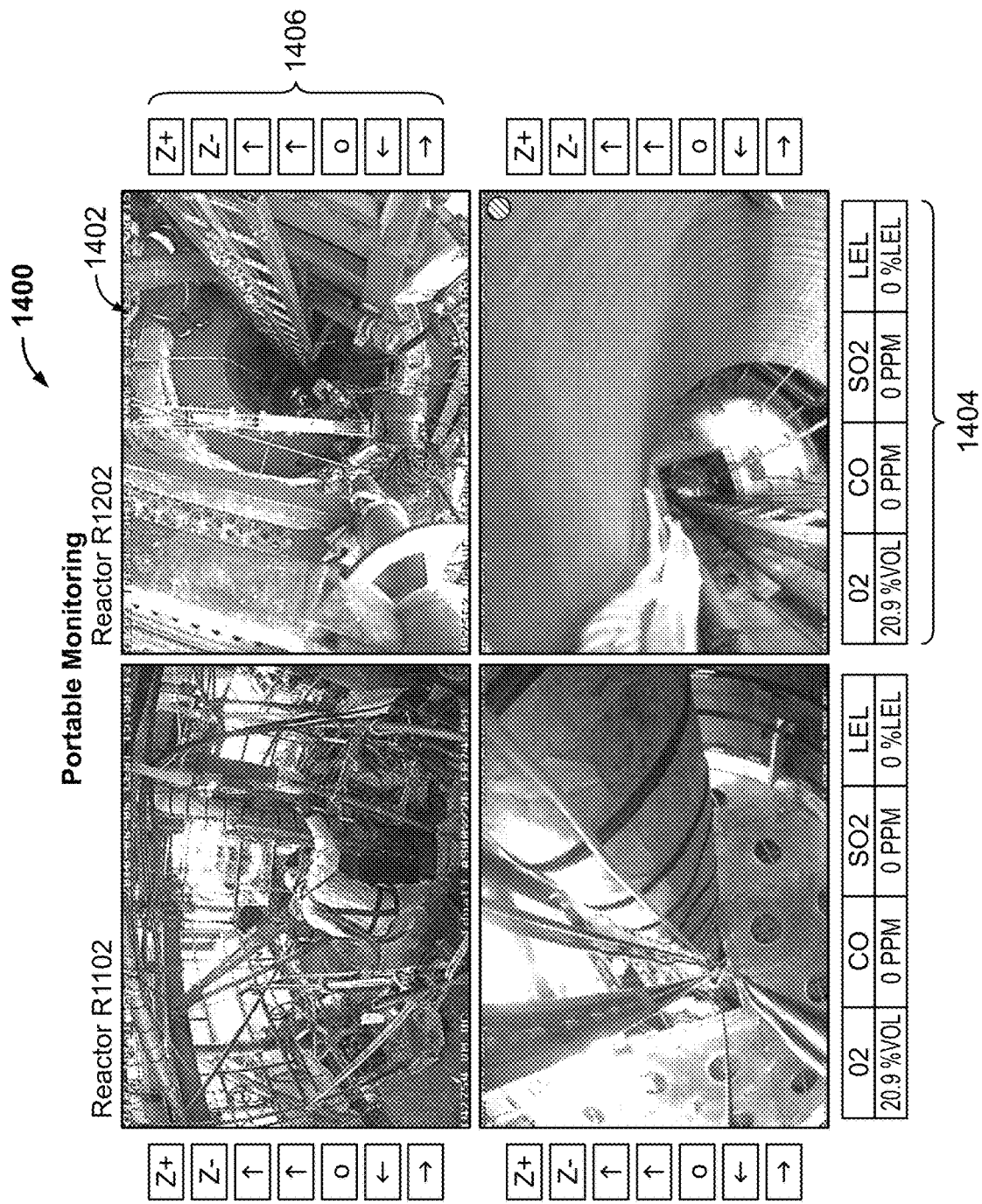
FIG. 14 show an example portable monitoring interface in accordance with one or more embodiments of the invention.

Another user interface of the confined space monitoring system is the portable interface accessible via the hub and point monitoring case from a user mobile device (e.g., as described above with reference to FIG. 1). FIG. 14 shows an example of the portable interface (1400). As shown in FIG. 14, the portable interface is a graphical user interface that is configured to be displayed on smaller devices than the local interface. The portable interface (1400) includes, for each confined space connected to the hub, a portion of the user interface for the confined space. The portion includes the camera feeds (e.g., camera feed (1402)), gas readings (e.g., gas readings (1404)), and control buttons (e.g., control buttons (1406)). The portable interface may include similar functionality to the web interface when a user selects various portions of the interface.

Figure 15A:
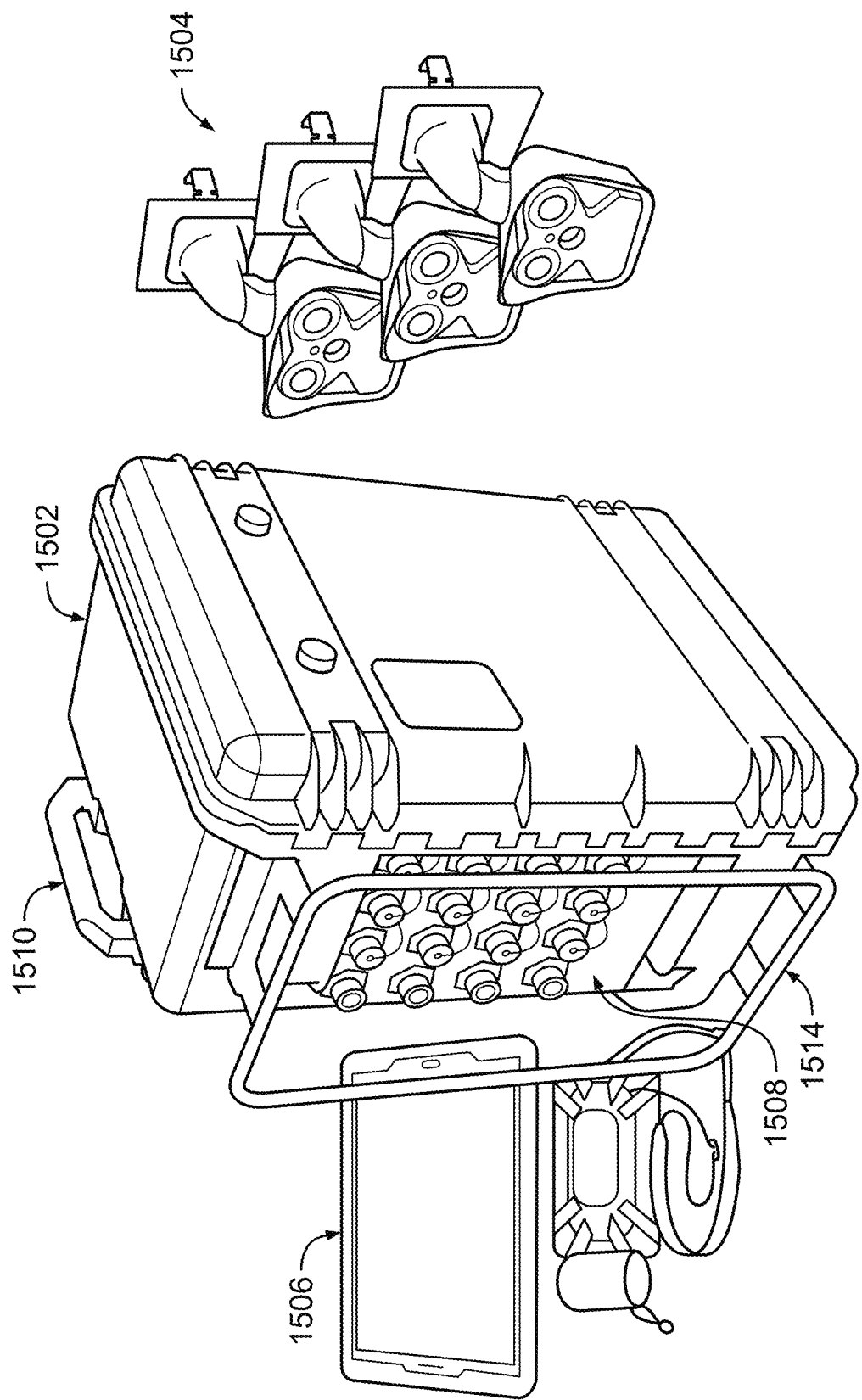
FIGS. 15A, 15B, and 15C show example confined space monitoring devices in accordance with one or more embodiments.
Figure 15B:
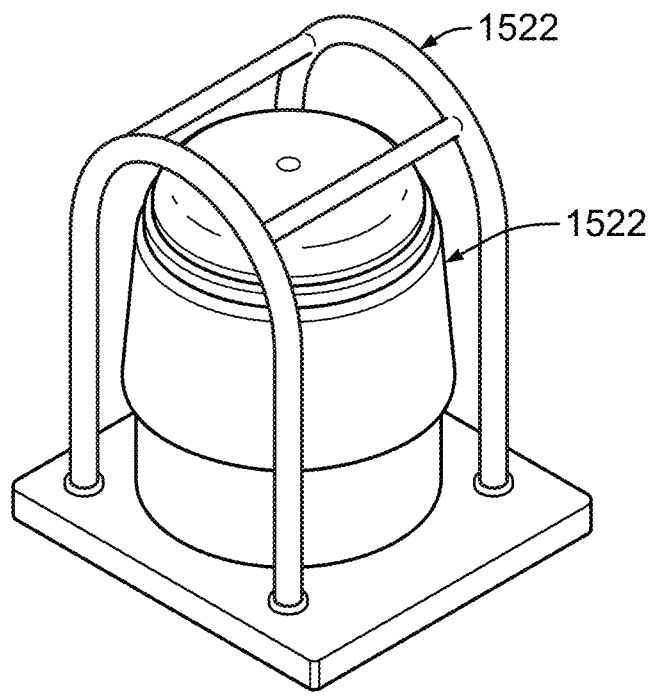
Figure 15C:
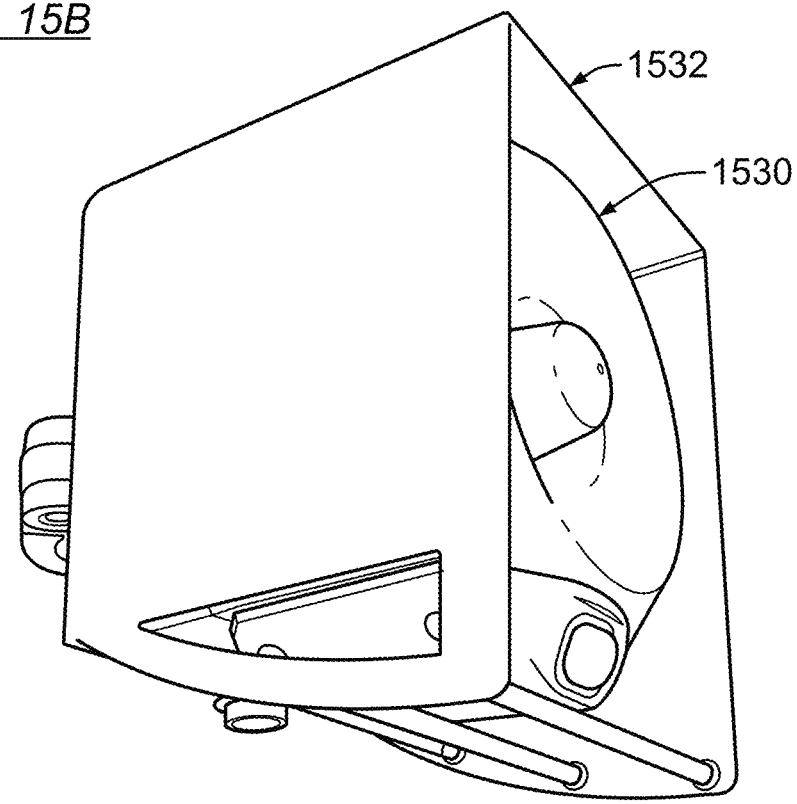

FIGS. 15A, 15B, and 15C show example confined space monitoring devices in accordance with one or more embodiments. FIG. 15A, shows the hub (1502), cameras (1504), and user mobile devices (1506). As shown in FIG. 15A, the hub is a condensed box that includes various ports (1508), and a handle (1510). The ports (1508) are protected via mechanical bar (1514) as shown in FIG. 15A. Inside the point monitor case are various computing system elements. The user mobile devices (1510) wirelessly connect to the hub (1502) and may obtain the portable interface (shown in FIG. 14) directly from the hub (1502). The portable interface on the user mobile devices (1510) include the gas detector measurement values and the camera feeds of the cameras (1504). Although FIG. 15 shows the hub, the point monitor case may have the same housing and ports. Thus, the point monitor case may have the same form factor as the hub shown in FIG. 15.

Other confined space monitoring devices include emergency lights, such as emergency light (1520) shown in FIG. 15B. As shown in FIG. 15B, the emergency light (1520) is encased in steel bars (1522) to prevent breakage while at the same time allowing for the dispersal of light. Similar mechanical protection may be used for the audio alarm (1530) as shown in FIG. 15C. Specifically, the audio alarm in FIG. 15 is encased in a steel housing (1532) that has an opening for the audio signal to travel. The above is a description of a few of the monitoring devices that may be used for the centralized confined space monitoring system. Other monitoring devices may be used without departing from the scope of the invention.

Figure 16A:
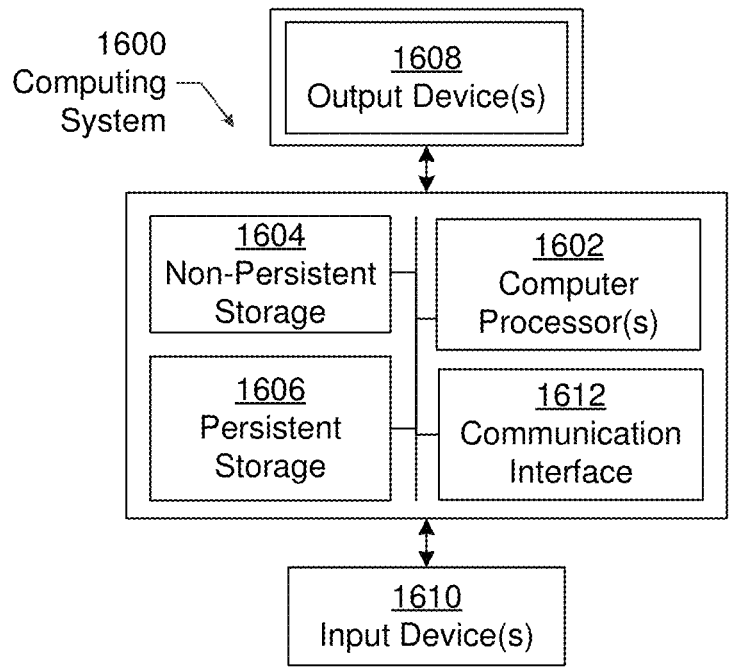
FIGS. 16A and 16B shows a computing device in accordance with one or more embodiments of the invention.

Embodiments of the invention may be implemented on a computing system. Any combination of mobile, desktop, server, router, switch, embedded device, or other types of hardware may be used. For example, as shown in FIG. 16A, the computing system (1600) may include one or more computer processors (1602), non-persistent storage (1604) (e.g., volatile memory, such as random access memory (RAM), cache memory), persistent storage (1606) (e.g., a hard disk, an optical drive such as a compact disk (CD) drive or digital versatile disk (DVD) drive, a flash memory, etc.), a communication interface (1612) (e.g., Bluetooth interface, infrared interface, network interface, optical interface, etc.), and numerous other elements and functionalities.

The computer processor(s) (1602) may be an integrated circuit for processing instructions. For example, the computer processor(s) may be one or more cores or micro-cores of a processor. The computing system (1600) may also include one or more input devices (1610), such as a touchscreen, keyboard, mouse, microphone, touchpad, electronic pen, or any other type of input device.

The communication interface (1612) may include an integrated circuit for connecting the computing system (1600) to a network (not shown) (e.g., a local area network (LAN), a wide area network (WAN) such as the Internet, mobile network, or any other type of network) and/or to another device, such as another computing device.

Further, the computing system (1600) may include one or more output devices (1608), such as a screen (e.g., light emitting diode (LED), a liquid crystal display (LCD), a plasma display, touchscreen, cathode ray tube (CRT) monitor, projector, or other display device), a printer, external storage, or any other output device. One or more of the output devices may be the same as or different from the input device(s). The input and output device(s) may be locally or remotely connected to the computer processor(s) (1602), non-persistent storage (1604), and persistent storage (1606). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

Figure 16B:
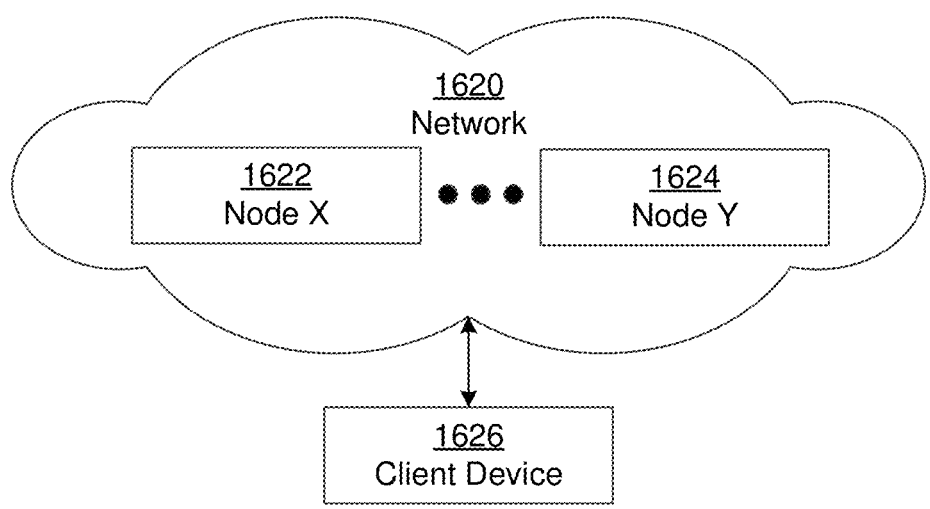

The computing system (1600) in FIG. 16A may be connected to or be a part of a network. For example, as shown in FIG. 16B, the network (1620) may include multiple nodes (e.g., node X (1622), node Y (1624)). Each node may correspond to a computing system, such as the computing system shown in FIG. 16A, or a group of nodes combined may correspond to the computing system shown in FIG. 16A. By way of an example, embodiments of the invention may be implemented on a node of a distributed system that is connected to other nodes. By way of another example, embodiments of the invention may be implemented on a distributed computing system having multiple nodes, where each portion of the invention may be located on a different node within the distributed computing system. Further, one or more elements of the aforementioned computing system (1600) may be located at a remote location and connected to the other elements over a network.

Although not shown in FIG. 16B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (1622), node Y (1624)) in the network (1620) may be configured to provide services for a client device (1626). For example, the nodes may be part of a cloud computing system. The nodes may include functionality to receive requests from the client device (1626) and transmit responses to the client device (1626). The client device (1626) may be a computing system, such as the computing system shown in FIG. 16A. Further, the client device (1626) may include and/or perform all or a portion of one or more embodiments of the invention.

The computing system or group of computing systems described in FIGS. 16A and 16B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the invention. The processes may be part of the same or different application and may execute on the same or different computing system.

Rather than or in addition to sharing data between processes, the computing system performing one or more embodiments of the invention may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the invention, may extract one or more data items from the obtained data. For example, the extraction may be performed as follows by the computing system in FIG. 16A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail-such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 16A, while performing one or more embodiments of the invention, may perform data comparison. Data comparison may be used to compare two or more data values (e.g., A, B). For example, one or more embodiments may determine whether A>B, A=B, A!=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the invention, A and B may be vectors, and comparing A with B requires comparing the first element of vector A with the first element of vector B, the second element of vector A with the second element of vector B, etc. In one or more embodiments, if A and B are strings, the binary values of the strings may be compared.

The computing system in FIG. 16A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 16A may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions presents only a few examples of functions performed by the computing system of FIG. 16A and the nodes and/or client device in FIG. 16B. Other functions may be performed using one or more embodiments of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:
1. A system comprising:
a plurality of confined space internal monitoring devices configured to acquire monitoring data from a confined space;
a point monitor case comprising a plurality of point monitoring case ports configured to be electrically coupled to the plurality of confined space internal monitoring devices;
a centralized monitoring station cabinet configured to be communicatively connected to the point monitor case, the centralized monitoring station cabinet comprising:
a display,
a processor, and
a centralized monitoring application configured to execute on the processor and comprising a local user interface, the local user interface comprising:
instructions, for each confined space of a plurality of confined spaces being monitored, the instructions including:
an instruction to display a number of workers in proximity to the confined space,
an instruction to display at least one camera feed from a camera located at a confined space,
an instruction to display a plurality of control buttons configured to control the plurality of confined space internal monitoring devices, and
an instruction to display a plurality of gas sensor indicators;
a hub communicatively interposed between the point monitor case and the centralized monitoring station cabinet, the hub comprising a wireless access point, an aggregator, and a graphical user interface, the graphical user interface configured to display, on a user mobile device, an aggregated current state comprising a combination of states of the plurality of confined spaces connected to the hub, the combination of states comprising a combination of data generated by the instructions; and wherein the aggregator is configured to aggregate a plurality of data streams from the plurality of point monitoring case ports connected to the plurality of confined space internal monitoring devices, the plurality of data streams generated by executing the instructions.

2. The system of claim 1, wherein the point monitor case comprises a user interface, the user interface comprising a visualization of a measurement acquired by at least one of the plurality of confined space internal monitoring devices.

3. The system of claim 2, wherein the user interface further comprises a control interface for the plurality of confined space internal monitoring devices.

4. The system of claim 1, further comprising:
a plurality of confined space external monitoring devices.

5. The system of claim 1, further comprising:
a plurality of confined space external monitoring devices connected to a plurality of point monitoring case ports of the point monitoring case, the plurality of confined space external monitoring devices comprising a panel housing of a single panel, wherein the panel housing comprises a badge reader, an intercom, and an alarm, wherein the plurality of confined space external monitoring devices are within line of sight to a confined space being monitored and outside of the confined space.

6. The system of claim 5, wherein the plurality of confined space internal monitoring devices comprises:
a panel housing of a single panel, wherein the panel housing comprises a badge reader, an intercom, and an alarm;
an air filter for acquiring an air sample;
an emergency light; and
a camera.

7. The system of claim 1, wherein the centralized monitoring station cabinet comprises:
a storage device comprising a data repository and a centralized monitoring application;
a primary touchscreen display device to display the local user interface; and
a computing processor.

8. The system of claim 1, wherein the local user interface comprises:
an instruction to display a test button configured to initiate a system test.

9. The system of claim 8, wherein the test button comprises a color indicator when a test is due.

10. The system of claim 1, wherein the plurality of control buttons comprises at least one button configured to remotely cause the camera to change a zoom amount of a lens of the camera.

11. The system of claim 1, wherein the centralized monitoring application comprises:
a web interface;
a plurality of software tools;
a plurality of user interface generation software components;
a plurality of services; and
a base component.

12. The system of claim 11, wherein the base component comprises:
a user interface logic layer;
a helper set;
a backend logic layer;
a plurality of data objects;
a gas detector connection; and
an access layer.

13. The system of claim 12, wherein the centralized monitoring application further comprises a plurality of services, and wherein the plurality of services comprises:
a camera image recorder;
a recording viewer;
a gas detector service;
an access panel service; and
a communication bus.

14. The system of claim 1, further comprising:
a testing interface configured to guide a user through performing a system test.

15. The system of claim 1, wherein the centralized monitoring application is configured to monitor a plurality of confined spaces, wherein each of the plurality of confined spaces has a unique section of the local user interface, wherein the plurality of control buttons are icons located to a right side of the at least one camera feed in the local user interface, wherein the number of workers are displayed above the at least one camera feed in the local user interface, and wherein the plurality of gas sensor indicators are displayed below the at least one camera feed.

16. The system of claim 1, wherein the point monitor case comprises a detachable mounting hook to mount the point monitor case on a structure in proximity to the confined space.

17. The system of claim 1, wherein the centralized monitoring station cabinet is foldable into box on a trolley.

18. The system of claim 1, wherein the plurality of confined space internal monitoring devices comprises:
an alarm surrounded by mechanical protection.

19. The system of claim 1, wherein the centralized monitoring station cabinet further comprises:
a network interface connection to connect to a plurality of point monitoring cases located in proximity to a plurality of confined spaces and connected to a plurality of confined space internal monitoring devices.

20. A method comprising:
receiving a data stream from a plurality of point monitoring cases proximate to a plurality of confined spaces, the data stream comprising at least one camera feed of the confined space; and
generating a display from the data stream for a single display device of a centralized monitoring station cabinet, wherein the display comprises a tile view comprising a tile for each confined space of the plurality of confined spaces being monitored, the tile comprising:
at least one camera feed from a camera located at the confined space;
a number of workers in proximity to the confined space, wherein the number of workers is displayed in the tile above the at least one camera feed;
a plurality of control buttons located in the tile to a right of the at least one camera feed; and
a plurality of gas sensor indicators located in the tile;
wherein a hub is communicatively interposed between the point monitor case and the centralized monitoring station cabinet, the hub comprising:
a wireless access point and a graphical user interface, the graphical user interface displaying, on a user mobile device, an aggregated current state of each confined space connected to the hub, the aggregated current state comprising the tile, and
an aggregator that aggregates a plurality of data streams from the plurality of point monitoring cases connected to a plurality of confined space internal monitoring devices, the plurality of data streams comprising the at least one camera feed, the number of workers, the plurality of control buttons, and the plurality of gas sensor indicators.

* * * * *